US011136551B2

(12) United States Patent
Braam et al.

(10) Patent No.: US 11,136,551 B2
(45) Date of Patent: Oct. 5, 2021

(54) IN VITRO METHOD OF DIFFERENTIATING A HUMAN PLURIPOTENT STEM CELL POPULATION INTO A CARDIOMYOCYTE CELL POPULATION

(71) Applicant: Ncardia B.V., Leiden (NL)

(72) Inventors: Stefan Robbert Braam, Leiden (NL); Ana Catarina Martins Grandela, Leiden (NL)

(73) Assignee: NCARDIA B.V., Leiden (NL)

( * ) Notice: Subject to any disclaimer, the term of this patent is extended or adjusted under 35 U.S.C. 154(b) by 0 days.

(21) Appl. No.: 15/756,083

(22) PCT Filed: Aug. 31, 2016

(86) PCT No.: PCT/NL2016/050609
§ 371 (c)(1),
(2) Date: Feb. 28, 2018

(87) PCT Pub. No.: WO2017/039445
PCT Pub. Date: Mar. 9, 2017

(65) Prior Publication Data
US 2018/0251734 A1    Sep. 6, 2018

(30) Foreign Application Priority Data

Sep. 1, 2015   (NL) .................................. 2015385

(51) Int. Cl.
*C12N 5/077*   (2010.01)

(52) U.S. Cl.
CPC ........ *C12N 5/0657* (2013.01); *C12N 2500/25* (2013.01); *C12N 2501/105* (2013.01); *C12N 2501/415* (2013.01); *C12N 2506/45* (2013.01)

(58) Field of Classification Search
CPC .................................................... C12N 5/0657
See application file for complete search history.

(56) References Cited

FOREIGN PATENT DOCUMENTS

| WO | 2014/078414 A1 | 5/2014 | |
|---|---|---|---|
| WO | WO-2014078414 A1 * | 5/2014 | .......... C12N 5/0657 |
| WO | 2015/040142 A1 | 3/2015 | |

\* cited by examiner

*Primary Examiner* — Thaian N. Ton
*Assistant Examiner* — David A. Montanari
(74) *Attorney, Agent, or Firm* — Browdy and Neimark, PLLC

(57) ABSTRACT

The current invention relates to a method of differentiation of human pluripotent stem cells into a human stem-cell derived population of cardiomyocytes. The method comprises the use of specific combination of steps and compounds to induce and/or promote differentiation. The method also comprises steps directed to further maturation of the cardiomyocytes obtained with the method of the invention. Also provided are kits for use in a method of differentiation as well as cell populations obtainable with the method disclosed.

28 Claims, 9 Drawing Sheets

Figure 1:
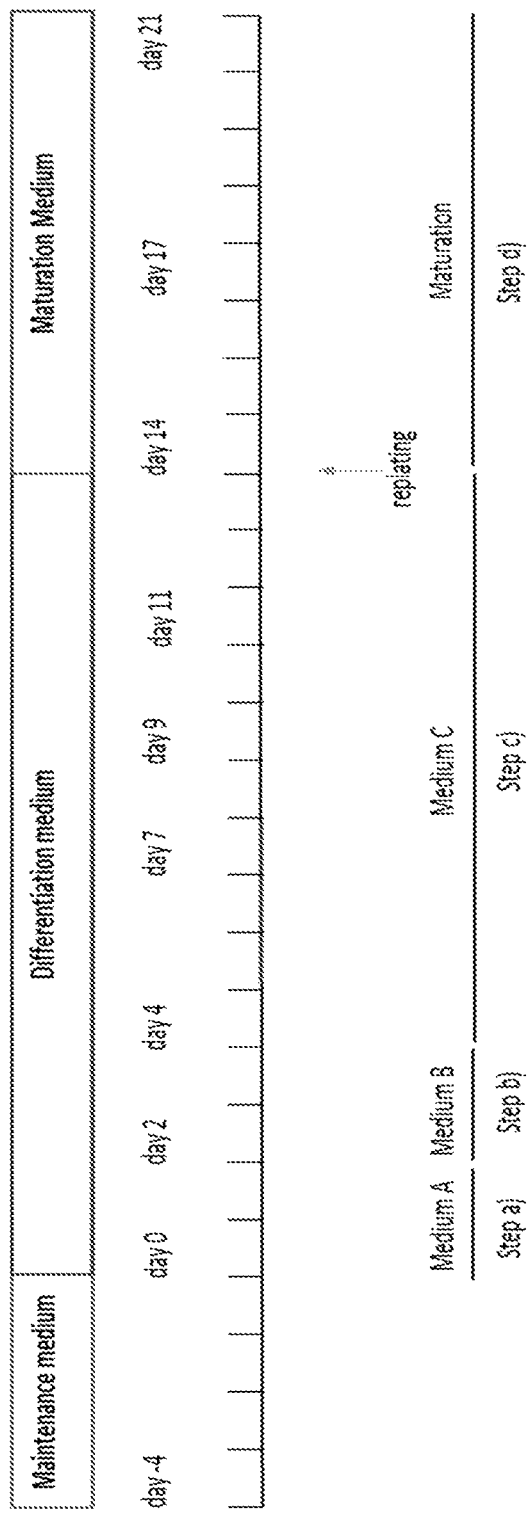

IN VITRO METHOD OF DIFFERENTIATING A HUMAN PLURIPOTENT STEM CELL POPULATION INTO A CARDIOMYOCYTE CELL POPULATION

CROSS-REFERENCE TO RELATED APPLICATIONS

This application is a U.S. National Stage filing under 35 U.S.C. § 371 of International Application No. PCT/NL2016/050609, filed Aug. 31, 2016, which in turn claims priority to Dutch Patent Application No. NL 2015385, filed Sep. 1, 2015, the entire contents of which are incorporated by reference herein.

PRIOR ART

Progress in several areas of medicine (i.e. mental health, cardiology, immunity etc.), where new and more effective drugs are needed, is severely impeded by the extreme cost engendered by lack of efficacy and undesired drug-induced adverse effects associated with several candidate lead compounds in the drug discovery pipeline. One major drawback of the current drug discovery process, for all drug development, is the high rate of attrition of lead compounds caused by lack of efficacy and unforeseen adverse drug effects, often detected in the later rather than in the earlier phases of the drug discovery pipeline.

Recent advances in pluripotent stem cell biology now make it possible to generate human cardiomyocytes in vitro from both healthy individuals and from patients with cardiac abnormalities. This offers unprecedented opportunities to study cardiac disease development 'in a dish' and establish novel platforms for drug discovery, to study mechanisms and molecules to prevent disease progression and to reverse it.

The prevention of drug-induced cardiotoxicity, which may manifest itself as cardiac arrhythmias, represents the highest priority for regulatory agencies and (bio)pharmaceutical companies, since manifestation of this type of toxicity is immediately life-threatening. It has been shown that 33% of adverse safety events in clinical studies are generally attributed to cardiac arrhythmic effects, which may lead to sudden death or severe cardiac complications in subjects (Mordwinkin et al (2013) Journal of cardiovascular translational research, Vol:6(1):22-30).

Therefore, there is an urgent need for new cost-effective strategies to improve the traditional process of drug development/discovery, e.g. eliminate drug-induced cardiotoxic effects. Particularly, there is an urgent unmet need for predicting drug-induced cardiotoxicity at an early stage in the drug pipeline development. Over the last decade, considerable research efforts have been devoted towards this goal. For instance, several biological models and tools have been developed including the use of pluripotent stem cells, ion-channel assays, and computational tools. Particularly, the use of cardiomyocytes derived from pluripotent stem cells is a current focus of interest in the development of innovative predictive assays to rectify the issues relating to cardiotoxicity during drug development. Pluripotent stem cells are a potential source of cells for generating cardiomyocytes in in vitro culture.

The use of cardiomyocytes is not only important for the development of assays for predicting drug-induced toxicity for all drugs in development, but is also important for cardiac research, target discovery and validation, as well as for the development of new cardiac drugs in general, where cardiomyocytes can be used to uncover new drug targets and assess cardiac drug safety.

The ability to use cardiomyocytes in drug development/discovery, drug safety assay, cardiac disease modelling, cardiac research, regenerative medicine and other biological purposes largely depends on the ability to cultivate and obtain cardiomyocytes derived from pluripotent stem cell culture in vitro.

In the art, various methods for producing and obtaining cardiomyocytes derived from pluripotent stem cell culture in vitro are known, recent examples of which include WO2014200339, WO2011056416, WO2015004539, WO2012026491 and WO2014078414.

At the same time, with regard to producing cardiomyocytes from pluripotent stem cells using in vitro cultivating techniques, it is generally accepted that the cardiac differentiation process is very delicate. Methods suitable for pluripotent stem cells of one species or source may not be suitable for others species or sources. Another problem is that compounds used to stimulate differentiation of the pluripotent stem cells are in often a-specific, in particular when relative high concentrations of such compound are required, modulating various targets (enzymes, signaling pathways) in the cell, both desired and undesired, which may in particular be problematic when more than one a-specific compound is used to differentiate the pluripotent stem cells.

For that reason there is a constant desire for improved methods of cultivating that allow for reproducible and robust in vitro production of human pluripotent stem cell derived cardiomyocyte cell populations. In particular there is need for methods that may be adopted for different sources of human pluripotent stem cells, including embryonic stem cells or various types of included pluripotent stem cells.

DESCRIPTION OF THE INVENTION

Definitions

Various terms relating to the methods, compositions, uses and other aspects of the present invention are used throughout the specification and claims. Such terms are to be given their ordinary meaning in the art to which the invention pertains, unless otherwise indicated. Other specifically defined terms are to be construed in a manner consistent with the definition provided herein. Although any methods and materials similar or equivalent to those described herein can be used in the practice for testing of the present invention, the preferred materials and methods are described herein "A," "an," and "the": these singular form terms include plural referents unless the content clearly dictates otherwise. Thus, for example, reference to "a cell" includes a combination of two or more cells, and the like.

"About" and "approximately": these terms, when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Adult-like cardiomyocytes" or "mature cardiomyocytes": This refers to cardiomyocytes which possess the desired phenotype and/or genotype in relation to an adult cardiomyocyte. In one embodiment, a mature cell has the phenotype and/or genotype of, but is not limited to, an adult cardiomyocyte or atrial cardiomyocyte or ventricular cardiomyocyte or SA nodal cardiomyocyte or peripheral SA nodal cardiomyocyte or central SA nodal cardiomyocyte. In other embodiments, adult-like cardiomyocytes or mature cardiomyocytes exhibit mature electrophysiology patterns and/or mature calcium handling patterns, and/or adult-type ion channel expression, and/or adult-type electrophysiological signals, and/or adult-like contractile properties, and/or adult-like gene expression patterns, and/or adult-type physical (morphological) phenotypes when compared to fetal-like (immature) cardiomyocytes derived from stem cells in vitro culture. Adult-like cardiomyocytes may also harbor greater degree of myofibril organization and sarcomere striations, which are features that are poorly or insufficiently developed in the foetal-like (immature) cardiomyocytes.

"Cardiomyocytes" or "cardiac myocytes": This refers to any cardiomyocyte lineage cells, and can be taken to apply to cells at any stage of cardiomyocyte ontogeny, unless otherwise specified. For example, cardiomyocytes may include both cardiomyocyte precursor or progenitor cells (i.e. cells that are capable, without dedifferentiation or reprogramming, of giving rise to progeny that include cardiomyocytes, e.g. immature cardiomyocytes or foetal cardiomyocytes) and mature cardiomyocytes (adult-like cardiomyocytes). Cardiomyocytes include atrial type cardiomyocytes, ventricular type cardiomyocytes, and/or conducting system cardiomyocytes (see e.g. Maltsev et al, Mech Dev. 1993 November; 44(1):41-50 or Cardiac Regeneration using Stem Cells (10 Apr. 2013); Keiichi Fukuda, Shinsuke Yuasa CRC Press. ISBN 9781466578401). The cardiomyocyte progenitors, like the mature cardiomyocytes, may express markers typical of the cardiomyocyte lineage, including, without limitation, cardiac troponin I (cTnI), cardiac troponin T (cTnT), sarcomeric myosin heavy chain (MHC), GATA-4, Nkx2.5, N-cadherin, β1-adrenoceptor (β1-AR), ANF, the MEF-2 family of transcription factors, creatine kinase MB (CK-MB), myoglobin, or atrial natriuretic factor (ANF).

"Comprising": this term is construed as being inclusive and open ended, and not exclusive. Specifically, the term and variations thereof mean the specified features, steps or components are included. These terms are not to be interpreted to exclude the presence of other features, steps or components.

"Conventional techniques" or "methods known to the skilled person": These terms refer to a situation wherein the methods of carrying out the conventional techniques used in methods of the invention will be evident to the skilled worker. The practice of conventional techniques in molecular biology, biochemistry, cell culture, genomics, sequencing and related fields are well-known to those of skill in the art and are discussed, for example, in the following literature references: Human Embryonic Stem Cell: The Practical Handbook. Publisher: John Wiley & Sons, LTD, Editors (Sullivan, S., Cowan, C. A., Eggan, K.) Harvard University, Cambridge, Mass., USA (2007); Human Stem Cell, a Laboratory Guide ($2^{nd}$ Edition) by Peterson, S., and Loring, J. F. (2012).

"Differentiating" and "differentiation": these terms, in the context of living cells, relate to progression of a cell further down the developmental pathway. A "differentiated cell" is a cell that has progressed further down the developmental pathway than the cell it is being compared with; differentiation is the process of progression. Human pluripotent stem cells can differentiate into lineage-restricted progenitor cells (cells that, like a stem cell, have a tendency to differentiate into a specific type of cell, but are already more differentiated than a stem cell and are pushed to eventually differentiate into its end-stage cell; e.g. endoderm, mesoderm and ectoderm), which in turn can differentiate into further restricted cells (e.g., cardiomyocyte progenitors, neuronal cell progenitors), which can differentiate into terminally differentiated cells (e.g., cardiomyocytes or neurons). Differentiation is controlled by the interaction of a cell's genes with the physical and chemical conditions outside the cell, usually through signaling pathways involving proteins embedded in the cell surface. In the present invention, "differentiation" is the biological process whereby an unspecialized human pluripotent stem cell (population) acquires the features of a specialized cell such as a cardiomyocyte under controlled conditions in in vitro culture. The human pluripotent stem cells may be exposed to the culture media compositions and methods of the invention so as to promote differentiation of the human pluripotent stem cells into (fetal-like) cardiomyocytes. Cardiac differentiation can be detected by the use of markers selected from, but not limited to, NKX2-5, GATA4, myosin heavy chain, myosin light chain, alpha-actinin, troponin, and tropomyosin (Burridge et al (2012) Stem Cell Cell, Vol. 10(1): 16-28, US2013/0029368). Within the context of the current invention, human pluripotent stem cell population are differentiated towards cardiomyocytes.

"Embryonic stem cells": abbreviated as 'ES cells' or ESC (or if of human origin 'hES cells' or 'hESCs') refers to stem cells that are derived from the inner cell mass of a blastocyst. The skilled person understands how to obtain such embryonic stem cells, for example as described by Chung (Chung et al (2008) Stem Cell Lines, Vol 2(2):113-117), which employs a technique that does not cause the destruction of the donor embryo(s). Various ESC lines are listed in the NIH Human Embryonic Stem Cell Registry. Pluripotent embryonic stem cells can be distinguished from other types of cells by the use of markers or lineage-specific markers including, but not limited to, Oct-4, Nanog, GCTM-2, SSEA3, and SSEA4.

"Exemplary": this terms means "serving as an example, instance, or illustration," and should not be construed as excluding other configurations disclosed herein.

"Fetal-like cardiomyocytes" or "immature cardiomyocytes": Cardiomyocytes derived from pluripotent stem cells in vitro culture, which does not (yet) possess the desired phenotype and/or genotype in relation to an adult or adult-like cardiomyocyte. Such immature cardiomyocytes may have the ability to differentiate into more mature cardiomyocytes. For instance such fetal-like (immature) cardiomyocytes may exhibit automaticity (spontaneous contraction) and/or fetal-type ion channel expression, and/or fetal-type electrophysiological signals, and/or fetal-like gene expression patterns, and/or fetal-type physical phenotypes. Fetal-like (immature) cardiomyocytes can be distinguished from other cell types by using markers or lineage-specific markers including, but not limited to, MYH6, TNNT2, TNNI3, MLC2V, EMILIN2, SIRPA, VECAM, and others markers suitable for assessing a fetal or fetal-like stage of development (Burridge et al (2012) Stem Cell Cell, Vol. 10(1):16-28, US2013/0029368).

"Induced pluripotent stem cell" or "iPSC": These terms refer to pluripotent stem cells that are derived from a cell that is not a pluripotent stem cell (i.e., from a cell this is differentiated relative to a pluripotent stem cell). Induced pluripotent stem cell can be derived from multiple different cell types, including terminally differentiated cells. Induced pluripotent stem cell generally have an ES cell-like morphology, growing as flat colonies with large nucleo-cytoplasmic ratios, defined borders and prominent nuclei. In addition, induced pluripotent stem cell may express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. Examples of methods of generating and characterizing induced pluripotent stem cells may be found in, for example, U.S. Patent Publication Nos. US20090047263, US20090068742, US20090191159, US20090227032, US20090246875, and US20090304646. To generate induced pluripotent stem cells, somatic cells may be provided with reprogramming factors (e.g. Oct4, SOX2. KLF4, MYC, Nanog, Lin28, etc.) known in the art to reprogram the somatic cells to become pluripotent stem cells (see, for example, Takahashi et. al, Cell. 2007 Nov. 30; 131(5):861-72; Takahashi et. al, Nat Protoc. 2007; 2(12): 3081-9; Yu et. al, Science. 2007 Dec. 21:318(5858):1917-20. Epub 2007 Nov. 20).

"Markers" or "lineage-specific markers": these terms refer to a characteristic associated with the phenotype of cells of a lineage and can be used to assess the differentiation of cells. The terms may for example refer to nucleic acid or polypeptide molecules that are differentially expressed in a cell of interest. The detectable level of the marker is sufficiently higher or lower in the cells of interest compared to other cells, such that the cell of interest can be identified and distinguished from other cells using any of a variety of methods known in the art.

"Media": This term refers to an aqueous solution, including buffers, suitable for maintaining human or animal cells for a sufficient period. For example, a media is suitable if it allows the treatment of cells for a period required to obtain the effect intended by the treatment. The term "media" also, and preferably, includes growth media that are suitable for the in vitro cell culture and/or differentiation of human or animal cells. A "defined media" refers to a (growth) media suitable for the in vitro cell culture of human or animal cells and in which all of the chemical components are known. Such defined media does not or essentially not comprise any ill-defined source of nutrients and/or other ill-defined factors. Within the context of the current invention the defined media used may still contain defined amounts of products such as (purified) albumin, growth factors, and hormones, but is essential free of serum (i.e. serum is less than 1% w/w, preferably less than 0.5% w/w. even more preferably less than 0.1% w/w, even more preferably less than 0.05% w/w of the media ready for use, most preferably the media is free of serum (i.e. 0% w/w serum; albeit it might contain defined amount of specified compounds like (recombinant) albumin. Although widely used, serum has many limitations. It contains high levels of numerous and unknown proteins and compounds which interfere dramatically with the small quantities of the desired proteins produced by the cells. The presence of serum may also affect in vitro testing results with the cells obtained since some compounds may bind up to 99% to serum proteins. Another limitation is the serum batch-to-batch inconsistencies, resulting in serious regulatory concern about various serum protein contaminations in the product.

"Pluripotency": This term is generally understood by the skilled person and refers to an attribute of a (stem) cell that has the potential to differentiate into all cells constituting one or more tissues or organs, for example, any of the three germ layers: endoderm (e.g. interior stomach lining, gastrointestinal tract, the lungs), mesoderm (e.g. heart, muscle, bone, blood, urogenital tract), or ectoderm (e.g. epidermal tissues and nervous system).

"Pluripotent stem cell" or "PSC": This is a stem cell capable of producing all cell types of the organism and can produce cells of the germ layers, e.g. endoderm, mesoderm, and ectoderm, of a mammal and encompasses at least pluripotent embryonic stem cells and induced pluripotent stem cells. Pluripotent stem cells can be obtained in different ways. Pluripotent embryonic stem cells may, for example, be obtained from the inner cell mass of an embryo. Induced pluripotent stem cells (iPSCs) may be derived from somatic cells. Pluripotent stem cells may also be in the form of an established cell line.

"Stem cells": Stem cells are a population of undifferentiated cells defined by their ability at the single cell level to both self-renew and differentiate to produce progeny cells, including self-renewing progenitors, non-renewing progenitors, and terminally differentiated cells (Morrison et al. (1997) Cell 88:287-298). Stem cells have the ability to divide for indefinite periods in culture. Stem cells are cells that may be stably multiplied and cultured in vitro and are totipotent, pluripotent, induced pluripotent, multipotent, oligopotent, or unipotent cells, preferably at least pluripotent. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts. Stem cells are categorized as somatic (adult) stem cells or embryonic stem cells. Stem cells may be characterized by both the presence of specific markers (e.g., proteins, RNAs, etc.) and the absence of specific markers. Stem cells may also be identified by functional assays both in vitro and in vivo, particularly assays relating to the ability of stem cells to give rise to multiple differentiated progeny.

"Stem cell-derived cardiomyocytes": These cells, or cardiomyocyte cell population, can be defined as spontaneously contractile cells derived by in vitro methods from a human pluripotent cell, although sometimes non-contractile cells can be obtained. Such cells still manifest other of the typical characteristics of cells that were in vitro differentiated into cardiomyocytes and are in the art also referred to as (in vitro obtained) stem-cell derived cardiomyocytes. Recent reviews defining and described stem-cell derived cardiomyocytes have covered methods to create (e.g. Vidarsson et al. Stem Cell Rev. 2010; 6(1):108-120, Boheler et al. Circ Res. 2002; 91(3):189-201. Mummery et al. Circ Res. 2012; 111(3):344-358, and Jiang et al. J Cell Mol Med. 2012; 16(8):1663-1668, David et al. Physiology (Bethesda) 2012; 27(3):119-129), and purify (Habib et al. J Mol Cell Cardiol. 2008; 45(4):462-474) such stem-cell derived cardiomyocytes, as well as their electrophysiology (Blazeski et al. Prog Biophys Mol Biol. 2012; 110(2):178-195), and these methods and media, for example based on APEL (StemCell Technologies) and StemPro34 (Invitrogen), used are well known to the skilled person.

"Somatic stem cell": an undifferentiated cell found in a differentiated tissue that can renew itself (clonal) and (with certain limitations) differentiate to yield all the specialized cell types of the tissue from which it originated.

"Undifferentiated": A stem cell that has not developed a characteristic of a more specialized cell is an undifferentiated cell. As will be recognized by one of skill in the art, the terms "undifferentiated" and "differentiated" are relative with respect to each other. A cells that is 'differentiated' has a characteristic of a more specialized cell. Differentiated and undifferentiated cells are distinguished from each other by several well-established criteria, including morphological characteristics such as relative size and shape, ratio of nuclear volume to cytoplasmic volume; and expression characteristics such as detectable presence of known (gene) markers of differentiation.

DETAILED DESCRIPTION OF THE INVENTION

It is an object of the current invention to provide an improved method of differentiating stem cells into cardiomyocytes, preferably ventricular cardiomyocytes It is a further object to provide for a method of differentiating human stem cells, in particular human pluripotent stem cells into cardiomyocytes, preferably ventricular cardiomyocytes.

It is an object to provide for a method that provides good yields of cells, preferably ventricular cardiomyocytes.

It is an object to provide for a method of differentiation human stem cells into cardiomyocytes, wherein the method is robust i.e. highly repeatable in/between independent tissue culturing methods, making the method reliable and suitable for use in production of cardiomycocytes, preferably ventricular cardiomyocytes, differentiated from human stem cells in vitro.

It is an object to provide for a method of differentiation human stem cells into cardiomyocytes, preferably ventricular cardiomyocytes, wherein the method is widely applicable to human stem cells obtained under different conditions (e.g. different cell lines) and/or previously (i.e. before differentiation of the stem cells) maintained in culture under various different conditions (e.g. using different methods or media for maintaining the human stem cells in an undifferentiated state).

It is an object to provide for a homogenous cardiomyocyte population, wherein a large part of the stem cells have differentiated into cardiomyocytes, preferably ventricular cardiomyocytes.

It is an object to provide for a method that provides cardiomyocytes, preferably ventricular cardiomyocytes, from stem cells within a relative short period of time.

It is an object to provide for a population of cardiomyocytes, preferably ventricular cardiomyocytes, wherein the population may be obtained with the method disclosed herein.

It is an object to provide for a method of differentiation of human pluripotent stem cells into or towards a cardiomyocyte population, preferably a ventricular cardiomyocytes population, wherein the method uses differentiation stimulating or promoting compounds at low concentrations or at concentrations that do no exert negative effect on the cells, such as toxicity, reduced yield or undesired alteration of phenotypical characteristics.

It is an object to provide for an in vitro method of supporting or enhancing the activity of XAV-939 as a inducer and/or stimulator of differentiation of human pluripotent stem cell towards a population of cardiomyocytes, preferably ventricular cardiomyocytes.

It is an object of the current invention to provide for a combination of compounds that, when used to contact human pluripotent stem cells, provides improved induction and/or stimulation of differentiation of human pluripotent stem cell towards a population of cardiomyocytes, preferably ventricular cardiomyocytes, preferably wherein the combination has no apparent adverse effect on the yield and or characteristics of the population of cardiomyocytes thus obtained.

It is an object of the current invention to provide for an in vitro method of differentiation of human pluripotent stem cells into a population of human stem-cell derived cardiomyocytes, preferably ventricular cardiomyocytes, that can be used for different sources of human pluripotent stem cells (e.g. obtained from different tissues or methods, cell lines, induced pluripotent stem cells).

It is an object to provide an improved in vitro method for differentiation of human pluripotent stem cell into cardiomyocytes that express mlc2v.

It is an object to provide an in vitro method for obtaining a population of ventricular cardiomyocytes from human pluripotent stem cells with high yield and within a relative short period of time (e.g. less than 35 days from plating the human pluripotent stem cells).

Other objects will become clear for the skilled person from the description, claims and examples provided herein.

These objects may be provided for with the method, use, compounds, products and kits of the current invention.

It is generally accepted that producing cardiomyocytes from pluripotent stem cells using in vitro cultivating techniques is very delicate, and the variability in each individual component of the cardiac differentiation strategy must be carefully optimized to reliably manufacture cardiomyocytes. Problems in the art relate to the robustness and repeatability of the process within one stem cell line and across a variety of lines. Specifically it has been reported that differentiation conditions have to be optimized for every specific line. In particular non-specificity of compounds used to induce or stimulate differentiation, and to interaction between such compounds, that may cause non-desired effects such as reduced yield of the cells, high variability in the progress of differentiation of cells within the cell population and/or altered phenotypical characteristics. In addition, when protein growth factors are used, the unpredictability of the stability of these factors may further complicate robustness of a given method.

It was found that with the method of the invention various of such problems may be circumvented, yielding a robust, reproducible and easy to apply method of differentiation of human pluripotent stem cells into a population of cardiomyocytes, preferably ventricular cardiomyocytes.

In a first aspect there is provided a method of differentiation of human pluripotent stem cells into cardiomyocytes, wherein the method is performed in vitro.

Provided is an in vitro method of differentiating a human pluripotent stem cell population into a cardiomyocyte cell population, the method comprising a step b), wherein step b) is contacting the human pluripotent stem cell population with XAV-939 and a second compound wherein the compound is IWP-L6 or C59 in an aqueous media.

It was found that a combination of XAV-939 and C59 can be advantageously used, in particular in the methods as described herein, to differentiate human pluripotent stem cells into cardiomyocytes, preferably ventricular cardiomyocytes.

It was further found that a combination of XAV-939 and IWP-L6 can be advantageously used, in particular in the methods as described herein, to differentiate human pluripotent stem cells into cardiomyocytes, preferably ventricular cardiomyocytes.

In the method human pluripotent stem cells are contacted with an amount of XAV-939 and a second compound wherein the compound is IWP-L6 or C59. XAV-939 and the second compound are provided to the cells in a concentration that is effective in inducing or promoting differentiation of the human pluripotent stem cells into or towards a population of stem-cell derived human cardiomyocytes. The skilled person understands that such concentration may, in view of the current disclosure, be determined using conventional techniques.

In the method, a population of human pluripotent stem cell is provided. The population of human pluripotent stem cells may be obtained from different sources. In the practice of the current invention the human pluripotent stem cells will be present in a vessel suitable for the cultivation of the human pluripotent stem cells under conventional conditions.

The human pluripotent stem cells are contacted with XAV-939 and the second compound present in a aqueous media. The skilled person understand that any type of media suitable for maintaining and/or cultivating the human pluripotent stem cells can be used, although, according to the invention, some media are more preferred (as disclosed herein).

The term aqueous media refers to a composition that is water-based or to a composition in which the solvent is water. For instance, an aqueous media can be obtained from dissolving (any) water-soluble substance(s) into water. Preferably the media is comprised with compounds and nutrients that support growth of the human pluripotent stem cells.

For the method of the invention it is not critical whether XAV-939 and the second compound are provided to the cells simultaneously or separately, i.e. as a combination or added to the media one at a time. It is also not critical whether the combination is already present in the media that is provided to the cell or added later, when the cell are already in the aqueous media.

The small molecule XAV-939, also known as 3,5,7,8-Tetrahydro-2-[4-(trifluoromethyl)phenyl]-4H-thiopyrano[4,3-d]pyrimidin-4-one is described by Huang et al., Nature. 2009 Oct. 1; 461(7264):614-20. XAV-939 is an inhibitor of beta-catenin-mediated transcription. XAV939 stimulates beta-catenin degradation by stabilizing axin, the concentration-limiting component of the destruction complex. XAV939 stabilizes axin by inhibiting the poly-ADP-ribosylating enzymes tankyrase 1 and tankyrase 2. XAV-939 may be obtained from various commercial sources.

The small molecule C59, or Wnt-c59, 2-[4-(2-methylpyridin-4-yl)phenyl]-N-(4-pyridin-3-ylphenyl)acetamide, was first disclosed in patent WO2010101849, and is an inhibitor of PORCN (Porcupine) with IC50 of 74 pM. C59 prevents palmitylation of Wnt proteins by Porcupine (a membrane-bound Oacyltransferase). C59 may be obtained from various commercial sources.

Figure 3:
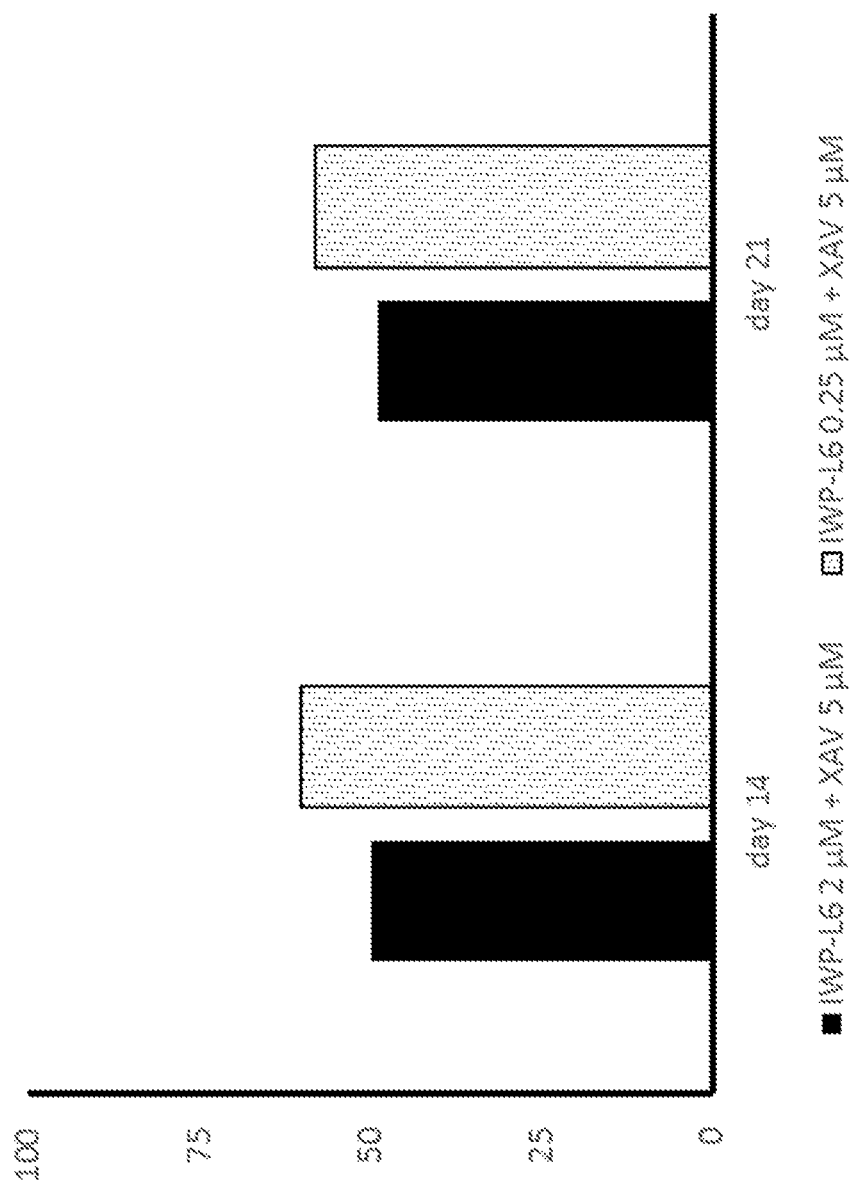

IWP-L6 (CAS no: 1427782-89-5), 2-[(4-oxo-3-phenyl-6,7-dihydrothieno[3,2-d]pyrimidin-2-yl)sulfanyl]-N-(5-phenylpyridin-2-yl)acetamide, is described in WO 2014186450, for example in FIG. 3, compound 27. IWP-L6 was found to suppress phosphorylation of dishevelled 2 (Dvl2) in HEK293 cells.

In one embodiment there is provided for the methods, use, kits and product of the invention wherein a combination of a tankyrase inhibitor and a porcupine inhibitor is used, exemplified by the combination of XAV-939 and the second compound (IWP-L6 and/or C59). The combination can be used in methods to achieve the objects disclosed herein, for example to induce and or stimulate differentiation of human pluripotent stem cells into a population of cardiomyocytes, preferably ventricular cardiomyocytes. Such combinations may have any of the advantages disclosed herein. In a preferred embodiment, the second compound is a found that suppresses phosphorylation of dishevelled 2 (Dvl2), in humans is encoded by the DVL2 gene.

In some preferred embodiments the method as disclosed herein further comprises a step a, that is performed prior to step b), and wherein in step a) the human pluripotent stem cell population is contacted with at least a Wnt-signaling agonist in an aqueous media.

In these embodiments, the human pluripotent stem cells are contacted prior to step b) with an amount of at least one Wnt-signaling agonist in a concentration that may be effective in inducing or promoting differentiation of the human pluripotent stem cells into or towards a population of stem-cell derived human cardiomyocytes, in particular in combination with the step b). Step a) causes the human pluripotent stem cells to differentiate into a population of mesodermal progenitor cell that, with the method of the invention, are capable of differentiating into cardiomyocytes. In other words, the concentration of the Wnt-signaling agonist in step a) further promotes the differentiation of the human pluripotent stem cells in the method of the invention, comprising step b). The skilled person understands that such concentration of the Wnt-agonist to be used in step a) may, in view of the current disclosure, be determined using conventional techniques.

In some embodiment the Wnt-signaling agonist may be combined with growth factors, including for example activin (e.g. activin A), bone morphologic protein (e.g. BMP-2 or BMP4), and/or combinations thereof.

Wherein in the application reference is made to at least a Wnt signaling agonist, in alternative embodiments, a combination of activin and a bone morphologic protein, preferably BMP-4 and/or BMP-2 is used instead of or in addition to the Wnt signaling agonist.

The human pluripotent stem cells are contacted with the Wnt-agonist in an aqueous media. The skilled person understand that any type of media suitable for maintaining and/or cultivating the human pluripotent stem cells can be used, although, according to the invention, some media are more preferred (as disclosed herein). The media is preferably identical to the media used in step b) except for the at least a Wnt-signaling agonist and the Xav-939/second compound combination.

For the method of the invention it is not critical whether the Wnt-signaling agonist is already present in the media that is provided to the cell or added later, when the cell are already in the aqueous media.

A Wnt signaling agonist may be any molecule that results in increased output from the Wnt signaling pathway, for example by stabilizing, enhancing the expression of, or enhancing the function of positive regulatory components of the pathway or by destabilizing, decreasing the expression of, or inhibiting the function of a negative regulatory components of the pathway. In particular GSK-3 has been shown to phosphorylate Beta-catenin, thus targeting it for degradation. For example a Wnt signaling agonist may inhibit GSK-beta, thus allowing nuclear levels of beta-Catenin to rise. For example, the Wnt signaling agonist is an inhibitor of GSK-3β, such as TWS119, BIO, CHIR-99021, SB 216763, SB 415286, CP21R7, CHIR-98014 and the like.

TWS119: 3-(6-(3-aminophenyl)-7H-pyrrolo[2,3-d]pyrimidin-4-yloxy)phenol is described by Ding et. al, Proc Natl Acad Sci USA. 2003 Jun. 24; 100(13):7632-7.

BIO: 6-bromo-3-[(3E)-1,3-dihydro-3-(hydroxyimino)-2H-indol-2-ylidene]-1,3-dihydro-(3Z)-2H-indol-2-one or (2'Z,3'E)-6-Bromoindirubin-3'-oxime is described by Meijer et. al, Chem Biol. 2003 December; 10(12):1255.66.

CHIR-99021: 6-[[2-[[4-(2,4-dichlorophenyl)-5-(5-methyl-1H-imidazol-2-yl)-2-pyrimidinyl]amino]ethyl]

amino]-3-pyridinecarbonitrile is described by Bennett et al., J Biol Chem. 2002 Aug. 23:277(34):30998-1004.

SB 216763: 3-(2,4-dichlorophenyl)-4-(1-methyl-1H-indol-3-yl)-1H-pyrrole-2,5-dione is described by Cross et al., J Neurochem. 2001 April; 77(1):94-102.

SB 415286: 3-(3-chloro-4-hydroxyphenylamino)-4-(2-nitrophenyl)-1H-pyrrole-2,5-dione is described by Cross et al., J Neurochem. 2001 April; 77(1):94-102.

CP21R7: (3-(3-Amino-phenyl)-4-(1-methyl-1H-indol-3-yl)-pyrrole-2,5-dione (CP21R7, described by Gong et al; Bioorganic & Medicinal Chemistry Letters 20 (2010), 1693-1696; also described in detail in EP2718425).

CHIR-98014: N2-(2-(4-(2,4-dichlorophenyl)-5-(1H-imidazol-1-yl)pyrimidin-2-ylamino)ethyl)-5 nitropyridine-2,6-diamine is described by Ring et al., Diabetes. 2003 March; 52(3):588-95.

The effective dose of a Wnt agonist may be at least about 0.1 microM. at least about 1 microM, at least about 2.5 microM, at least about 5 microM, and usually not more than about 500 microM, not more than about 250 microM, not more than about 100 microM, not more than about 50 microM. In some embodiments the effective amount is around about 5 microM.

Preferably, CHIR-99021 is used in the method of the invention, preferably is a concentration of 0.1 microM-50 microM, more preferably in a concentration of 0.5-20 microM, even more preferable in a concentration of 0.5 microM-10 microM; in a in particular preferred embodiment CHIR-99021 is used in a concentration of 4-7 microM.

In some preferred embodiments, CHIR-99021 is used as the Wnt-signaling agonist step a) and XAV-939 and IWP-L6 is used in step b).

In some embodiments, the method further comprises contacting the human pluripotent stem cell population with IGF, preferably long range IGF in an aqueous media. It was surprisingly found that adding IGF to the aqueous media may improve yield of cardiomyocyte cells, in comparison to the same method and wherein in IGF was employed.

Insulin-like-growth-factor (IGF) as used herein comprise both IGF-1, and IGF-2, which are well-known members of the insulin superfamily of hormones, growth factors and neuropeptides. The insulin-like-growth-factor and growth hormone (GH) axis plays a large part in regulating fetal and childhood somatic growth. Insulin like growth factor-I is also known as somatomedin C.

IGF-1 is a hormone similar in molecular structure to insulin. It plays an important role in childhood growth and continues to have anabolic effects in adults. A synthetic analog of IGF-1, mecasermin, is used for the treatment of growth failure. The major role of IGF-2 is as a growth promoting hormone during gestation. The growth factor has a major, but not absolute, dependence on somatotropin.

Also comprised by the term are recombinant analogs of insulin-like growth factor, for example recombinant analogs of human insulin-like growth factor, such as long range IGF-1, i.e. a recombinant IGF-1 with increased potency and/or durability for using during cultivation. One example is LONG® R3 IGF-I, which is a recombinant analog of human insulin-like growth factor-I (IGF-I) that has been specifically engineered for the enhancement of cell culture performance. It is more biologically potent in vitro than either insulin or native IGF-1 and has been shown to significantly increase recombinant protein production. It is ideal for culture systems utilizing serum-free or low-level serum applications (see, for example, Hussain Dahodwala et. AI Cytotechnology, 64(1), 27-41 (2012) and U.S. Pat. Nos. 5,330,971, 5,164,370, and EP429586; obtainable from repligen www.repligen.com/cell-culture-growth-factors/long-r3igf-i)./PCT IGF may be added during any stage of the method of differentiating the human pluripotent stem cell population. IGF may, for example, be provided to the human pluripotent stem cell population immediately after plating or passaging the cells (i.e. after transferring of a small number of cells into a new vessel for cultivating) and before, for example, step a) is performed (the contacting of the cells with at least the Wnt-signaling agonist), or before step b) is performed (the contacting of the cells with XAV-939 and IWP-L6 and/or C-59). It was however surprisingly found that IGF may also be provided to the cells during step a) or step b), i.e. simultaneously with contacting the cells with at least the Wnt-signaling agonist or with XAV-939 and IWP-L6 and/or C-59. The presence of IGF during step a) or b) surprisingly did not negatively influence differentiation of the human pluripotent stem cells into a cardiomyocyte cell population (i.e. the rate or progress of differentiation), whereas it does improve the total amount of cells that may be obtained. It was thus surprisingly found that IGF does not negatively interact with the compounds used in the method of the invention to induce or promote differentiation of the human pluripotent stem cells (including, for example insulin, when used at any stage). IGF may also be provided to the human pluripotent stem cells after step b) is performed, i.e. after the cells have been contacted with XAV-939 and IWP-L6 and/or C-59. IGF may be present during any stage or step of the method of differentiating the human pluripotent stem cell population.

The aqueous media used may be any suitable media for maintaining and or differentiating the human pluripotent stem cells with the method disclosed herein.

Providing IGF to the human pluripotent stem cells in a suitable concentration may be done using conventional techniques, and may include refreshing the media during the cultivation.

In some embodiments, when IGF, including long range IGF, is used, the aqueous media wherein the IGF is present does not comprise any insulin, or any insulin and any transferrin, or any insulin and any transferrin and any selenium. In another embodiment, no insulin, or no insulin and transferrin, or no insulin and transferrin and selenium are used in the method of the invention when IGF is used.

Insulin, transferrin and selenium are well-known in the art and are commercially available. A non-limiting example of commercially available preparation comprising insulin, transferrin and selenium is Gibco's Insulin-Transferrin-Selenium Ethanolamine Solution (ITS-X) preparation (catalogue #51500, quantity: 10 mL), which is characterized in that it contains 1000 mg/L (0.17 mM) of insulin, 550 mg/L (6.87 mM) of transferrin, 0.67 mg/L (0.0038 mM) of sodium selenite, 200 mg/ml (3.27 mM) of ethanolamine.

In some embodiments, the method of the invention further comprises a step c) of contacting, after step b), the human pluripotent stem cell population with an aqueous media not comprising XAV-939, said second compound, and/or said Wnt-signaling agonist, preferably wherein the aqueous media comprises IGF. It was found that it is not necessary to contact the human pluripotent stem cells in step b) with the combination of XAV-939 and the second compound (C59 and/or IWP-L6), during the whole period the cells are differentiated into a population of stem-cell derived cardiomyocytes.

In fact, cultivating the cells in the absence of such combination, after a certain period of treatment with such combination in step b) (e.g. using periods of contacting as described below), gave homogenous cardiomyocyte populations with high yield, in particular when in the method of the invention the cells were also contacted with IGF, for example, when the cells where contacted with IGF after step b) and in the media that is devoid of other compounds intended to induce or promote differentiation of the human pluripotent stem cells, such as a Wnt-signaling agonist and/or Wnt-signaling antagonist. The aqueous media used may be any suitable media for maintaining and or differentiating the human pluripotent stem cells with the method disclosed herein and providing such media and cultivating the cells may be done by the skilled person using conventional techniques, which includes, for example cultivating at permissible temperatures and, if desired, refreshing of the media.

The second compound used in the method of the invention may be IWP-L6 and/or C59. However, in a preferred embodiment the compound that is combined with XAV-939 is IWP-L6. It was found that IWP-L6, when combined with XAV-939 allows for better differentiation of the human pluripotent stem cell population into a cardiomyocyte cell population, preferably a ventricular cardiomyocytes cell population. Relative to IWP-L6, the concentrations of C59 employed in the combination with XAV-939, was observed to provide a reduced yield of cell obtained with the method of the invention (data not shown). In other words, relative to IWP-L6, C59 appears, in the combination with XAV-939, more toxic to the human pluripotent stem cells. In addition, it was surprisingly found that the concentration of IWP-L6 may be considerably low(er), making IWP-L6 in particular useful in the method of the invention, as the low concentration may reduce a-specific and undesired side-effects. Therefore, in a preferred embodiment the second compound in the combination with XAV-939 is IWP-L6. It was surprisingly found that the combination of XAV-939 and IWP-L6 is an efficient combination for inducing or promoting differentiation of the human pluripotent stem cell population into a cardiomyocyte cell population, preferably a ventricular cardiomyocytes cell population, in comparison to another such combination.

Moreover, the beneficial effect of the specific combination of XAV-939 and IWP-L6 was found for all different sources of human pluripotent stem cells tested and thus appears independent of the cell lines used in the method of the invention.

In addition, and importantly, it was surprisingly found that the advantages of the method of the invention, comprising the use of the combination of XAV-939 and the second compound, preferably IWP-L6, are also independent of the method used (before performing step b), or, when step a) is performed, step a)) to maintain the human pluripotent stem cells in the undifferentiated state (e.g. using such maintenance methods tested as E8, feeders, mTeSR, and L7, see examples), and thus appears source independent. In practice, before cells are subjected to differentiation, the human pluripotent stem cells are, for example, upon passage of the cells, or seeding of the cells, cultivated in a maintenance medium, substantially keeping the human pluripotent stem cells in an undifferentiated state. It was found surprisingly found that the method used for maintenance of the cells before differentiation is induced with the method of the invention may be any suitable method, further proving the robustness and general applicability of the method of the invention. In fact, the current inventors observed that the maintenance period (i.e. the period of cultivating the undifferentiated human pluripotent stem cells in a medium), may be reduced in time in comparison to the same differentiation method and where the combination of XAV-939 and the second compound, preferably IWP-L6, is not used.

An example of a suitable media for maintenance of the cells would be DMEM/F12 (Gibco, cat. no. 11320-033), 1-30%, preferably 15-25, more preferably about 20% (v/v) knockout serum replacement (e.g. Gibco, cat. no. 10828-028), 0.01-1, mM, preferably 0.05-0.5 mM, more preferably about 0.1 mM non-essential amino acids (e.g. 1× Gibco, cat. no. 11140-050), 0.1-10 mM, preferably 0.5-5 mM, more preferably about 2 mM L-glutamine (e.g. Gibco, cat. no. 25030-081), optionally 2b-mercaptoethanol (e.g. Gibco, cat. no. 21985-023), and 0-40, preferably 1-20, more preferably about 10 ng/ml human bFGF (fibroblast growth factor-basic). But, as is clear from the above, any suitable media may be initially used.

In some preferred embodiments, the media used as the media for differentiation in the method (i.e. used as the base media in step a), b), and/or c), and possibly d)) is essentially serum free, and preferably the media comprises lipids and one or more trace elements, and optionally insulin, transferrin and selenium.

In a preferred embodiment in the methods of the invention for obtaining cardiomyocytes, in particular ventricular cardiomyocytes, the media in step b) does not comprise vitamin A and/or derivatives thereof (e.g. retinoic acid, retinol, retinal, provitamin A carotenoids, and the like).

In a further preferred embodiment in the methods of the invention for obtaining cardiomyocytes, in particular ventricular cardiomyocytes, the media in steps a), b) and/or c) does not comprise vitamin A and/or derivatives thereof (e.g. retinoic acid, retinol, retinal, provitamin A carotenoids, and the like). In these embodiments, also step d) (if performed) may be performed with or without vitamin A and/or derivatives thereof (e.g. retinoic acid, retinol, retinal, provitamin A carotenoids, and the like).

Within the context of the current invention a media is essentially serum free when the percentage of serum is less than 1% w/w, preferably less than 0.5% w/w, even more preferably less than 0.1% w/w, even more preferably less than 0.05% w/w of the media ready for use, most preferably the media is free of serum (i.e. 0% w/w serum). By definition, essentially serum-free media essentially lacks whole serum as an ingredient, but it may not be entirely free of serum-derived products, for example highly purified form of albumin, for example bovine or even human (recombinant) albumin may be included in such serum-free media. For example, it may comprise up to 10 wt %, preferably up to 5 wt %, even more preferably up to 2 w %, up to 1 wt %, up to 0.5 wt %, or most preferably up to 0.25 wt % albumin, e.g. Bovostar BSA from Bovogen (Williams Ave Keilor East VIC 3033, Australia). A media essentially free of serum, may, in the context of the current invention be a defined media. Preferably the media used in the method of the invention is a defined media.

The skilled person understand that at different stages of the method, for example, the media used in step a), step b) and/or step c), or step prior or after said steps may or may not be essentially serum free. For example, the cells may or may not initially be plated in a media comprising serum.

In a preferred embodiment a defined media is used in one or more, preferably all steps of the method of the invention. Such defined media may be any media suitable for maintenance of the human pluripotent stem cells, for example any media suitable to cultivate the human pluripotent stem cells.

Chemically defined serum-free culture media are well-known in the art and are commercially available. The skilled person in the art knows how to select an appropriate (chemically defined) serum-free culture media for the preparation of the culture media compositions of the invention. Non-limiting examples of commercially available and (chemically defined) serum-free basal culture media include, F-12 nutrient mixture (Ham), F-10 nutrient mixture, Leibovitz L-15, McCoy's 5A, MCDB 131, G-MEM, Improved MEM, DMEM, DMEM/F12, RPMI-1640, Waymouth's MB 752/1, Williams' Media E, IMDM, Media 199, Opti-MEM, Modified Eagle, Media (MEM), Minimal Essential Media (MEM), BGJb (Fitton-Jackson Modification), CMRL, BME. Mixture of one or more chemically specified serum-free media can be employed in the culture media compositions of the present invention. A non-limiting example of a mixture of two chemically specified serum-free culture media is for instance a mixture comprising IMDM and F12 nutrient (Ham). Said mixture was shown to be particularly suitable for the preparation of the culture media compositions of the present invention.

For instance in the present invention, the basic differentiation media composition suitable to differentiate undifferentiated human pluripotent stem cells into cardiomyocytes is a medium composition that is serum-free, comprises a basal medium, (recombinant) albumin, and optionally ascorbic acid (e.g. from 20-70 microgram per ml/for example about 50 microgram per ml), and may further comprise a lipid mixture, insulin, transferrin and selenium, and one or more trace elements (e.g. one or more elements, preferably all, selected from the group of Mn, Si, Mb, V, Ni, Sn, AL, Ag, Ba, K, Cd, Co, CR, F, Ge, I, Rb, and Zr).

For example, the differentiation media contains 40-50%, for example 46.5% IMDM (Gibco 21056), 0-1%, for example 0.25% Bovostar BSA, 40-50%, for example 46.5% Ham's F12 with Glutamax, 0.1-4 mM, for example 2 mM Glutamax, 350-550 nM, for example 450 nM alphaMTG, 0-0.2 mg/ml, for example 0.05 mg/ml ascorbic acid, 0-1%, for example 0.5% 5000 U/ml Pen/Strep (Gibco 12070), 0.005-0.02, for example 0.01% 1000* Trace elements mix B (Cellgro 99-176-CL), 0.005-0.02, for example 0.1% 1000* Trace elements mix C (Cellgro 99-176-CL).

The differentiation media may further comprise a mixture of lipids. The mixture of lipids may comprises cholesterol (e.g. about 1 microgram/ml to about 4 microgram/ml) and one or more lipids selected from linolenic acid, linoleic acid and palmitic acid (for example 0.001-1 microgram/ml of any lipid, preferably 0.01-1 microgram/ml, even more preferable 0.05-2 microgram/ml, for example about 0.1 microgram/ml of linoleic acid and/or linolenic acid, and/or palmitic acid), and optionally arachidonic acid, DL-alpha-tocopherol acetate, ethyl alcohol, myristic acid, oleic acid, palmitoleic acid, pluronic F-68, stearic acid, and tween 80. For example, 0.05-2%, for example 1% (w/w or vol/vol) 100*Chemically defined lipids (Gibco 11905).

The differentiation medium may further comprise about 0.05-3, preferably 0.1-2, even more preferable about 0.5-1.5 mg/L, and/or about 0.01-2 mg/L, preferable about 0.1-1 mg/L, even more preferable about 0.25-0.75 mg/L transferrin, and/or about 0.0001-0.01 mg/L, preferably about 0.0004-0.0008 mg/L, for example about 0.0005-0.0007 mg/L of selenium and/or about 0.1 mg/L to about 5 mg/L of insulin, preferably about 0.3 mg/L to about 4 mg/L of insulin, preferably about 0.5 mg/L to about 3 mg/L of insulin, preferably about 0.7 mg/L to about 2 mg/L of insulin, preferably about 0.9 mg/L to about 1.2 mg/L of insulin, preferably about 0.95 mg/L to about 1.05 mg/L of insulin, more preferably about 1 mg/L of insulin. For example 0.1% 100* ITS-X (Gibco 51500).

The differentiation medium may further comprise polyvinylalcohol (PVA), typically is concentrations of about 0.012-0.5% by weight, preferably about 0.05-0.2% by weight, for example about 0.125% by weight (also any media used to mature the cells may comprise such amounts of PVA).

In embodiments wherein IGF is used in the method of the invention, the media used may or may not comprise any insulin, or any insulin and any transferrin, or any insulin and any transferring or any selenium, as already discussed above, either in the media comprising IGF or in any media used in the method of the invention.

Such media as described above is a in particular suitable media for cultivating the human pluripotent stem cells during step a), b) and c) of the method of the invention.

Conventional techniques may be employed by the skilled person in providing the human pluripotent stem cells with a suitable media and under conditions that allow for the maintenance and growth of the human pluripotent stem cells in the media.

The skilled person understands that the period during which the human pluripotent cell population is contacted during the various steps of the method of the invention should be of sufficient length for allowing the cells, in the method of the invention, to differentiate into a cardiomyocyte cell population, preferably a ventricular cardiomyocyte cell population. The skilled person can, using conventional techniques, to establish such suitable periods.

However, in some embodiments, and wherein step a) is performed, preferably step b) is initiated at least 1 and up to 7 days after initiation of step a) and/or wherein said step b) is concluded within 35 days, preferably within 14 days, more preferably within 5 days, even more preferably within 3 days, most preferably within 2 days after its initiation. Preferably step b) is at least performed for two days. In an embodiment, step a) is performed for 2 days and step a) is performed for 2 days.

It was surprisingly found that employing such lengths for the period of step a) and of step b), in particular when the combination employed in step b) is XAV-939 and IWP-L6, gives well-differentiated population of cells.

The skilled person understand that within the context of the current invention that the contacting in step a) and step b) are not performed simultaneously or in an overlapping manner. Step b) follows is performed after step a) has been performed. This prevent that XAV-939 and the second compound employed in step b) is present at the same time as the Wnt-signaling compound in step a). The skilled person understand that between step a) and step b) there may be a short period of cultivating the cells before starting step b). However, it is preferred such period is no longer than 3 days, preferably no longer than 1 day, most preferably absent.

Thus, in some embodiment step a) is performed for at least 1 day, preferably 1-7 days, for example 1, 2, 3, 4, 5, 6, or 7 days. Thus is some embodiments, step b) is performed for at least 1 day, preferably 1-35 days, for example 1-14 days, 1-5 days or 1-2 days, for example 1, 2, 3, 4, 5, . . . 35 days.

In embodiments wherein step a) is not performed (i.e. wherein the human pluripotent stem cell are not contacted with a Wnt-signaling agonist prior to the cells being contacted with the combination of XAV-939 and the second compound (C59 and/or IWP-L6), step b) is performed for at least 1 day, preferably 1-35 days, for example 1-14 days, 1-5 days or 1-2 days, for example 1, 2, 3, 4, 5, . . . 35 days.

In some preferred embodiments, and wherein step c) is performed, step c) is concluded within 35 days, preferably within 28 days, more preferably within 21 days, even more preferably within 14 days, most preferably within 10 after its initiation. It was found that with the method of the invention, the time required to obtain a population of cardiomyocytes can be reduced. Preferably the period of step c) is at least 1 day, for example between 1-35 days, preferably between 1-14 days, for example, 1, 3, 4, 6, 7, 8, 9, 10, 11, 12, 13, or 14 days.

In some embodiments, the period of cultivating the cells with the method of the invention (until the end of step b) or step c)) is within 21 days, for example between 5-21 days, preferably between 7-15 days, for example 12-14 days.

The skilled person understands that the concentration of the various compounds used in the method of the invention may vary, depending for example, on the source of human pluripotent stem cell used and/or the specific conditions used for cultivating the cells. The skilled person can, using conventional techniques, establish such suitable concentration.

However, one of the advantages of the method of the invention is that concentrations of compounds may be used to induce and/or promote differentiation of the human pluripotent stem cells that an efficient and, in particular in the combination, do not exhibit negative effects on differentiation or yield of the cells (for example, by acting a-specifically of various targets (enzymes/proteins and the like) in the cell).

Therefore in advantageous embodiments of the method of the invention, the concentration XAV-939 is 0.1-20 microM in the aqueous media.

Therefore in advantageous embodiments of the method of the invention, the concentration C-59 is 0.05-0.50 microM in the aqueous media.

Therefore in advantageous embodiments of the method of the invention, the concentration IWP-L6 is 0.01-15 microM in the aqueous media.

Therefore in advantageous embodiments of the method of the invention, the concentration IGF is 0.01-10 ng/ml in the aqueous media. In some embodiments, wherein IGF is present in the aqueous media, the aqueous media or any other aqueous media used in the method does not comprise insulin or insulin and transferring or insulin and transferring and selenium.

Preferably, and when the compound is employed in the method of the invention, the concentration XAV-939 is 0.1-20 microM in the aqueous media, the concentration C-59 is 0.05-0.50 microM in the aqueous media, the concentration IWP-L6 is 0.01-15 microM in the aqueous media and the concentration IGF is 0.01-10 ng/ml in the aqueous media.

Providing the compounds to the human pluripotent stem cells in a suitable concentration may be done using conventional techniques, and may include refreshing the media during the cultivation.

Independent of the concentration used, it was surprisingly found that, where the second compound is IWP-L6, the ration between XAV-939 and IWP-L6 used in the combination of compounds in step b) is preferably (XAV-939:IWP-L6) between 1:1 and 1:0.001, more preferably between 1:0.1 and 1:0.01, even more preferably between 1:0.2 and 1:0.8, even more preferably about 1:0.05. It was found that the more preferred ratios of XAV-939:IWP-L6 give homogenous populations of cardiomyocytes (for example, a large part of the human pluripotent stem all show, after cultivating with the method of the invention, characteristics of (mature or immature) cardiomyocytes, preferably ventricular cardiomyocytes, whereas at the same time the cells are provided with high yield, making the method of the invention robust, highly repeatable and, as mentioned before, usable for all kinds of sources of the human pluripotent stem cells employed.

In a particularly preferred embodiment of the method of the invention, the concentration of XAV-939 with which the human pluripotent stem cell population are contacted in step b) is a concentration, the increase of which will not further stimulate differentiation of the human pluripotent stem cell population in the absence of the second compound. In this embodiment, the concentration of XAV-939 used in the method of the invention is a concentration that when the concentration thereof would be increases and used alone in the method of the invention (i.e. not in combination with the second compound, in particular IWP-L6), would not further stimulate differentiation of the human pluripotent stem cell population into cardiomyocytes, preferably ventricular cardiomyocytes, and for example a measured based on a cardiomyocyte marker as discussed herein. For example, if increase of a certain concentration X to a concentration X+Y does not further increase, under similar conditions, the differentiation of the human pluripotent stem cells into cardiomyocytes (and in the absence of the second compound (C59/IWP-L6), as measured by the number of e.g. TNNT2-positive cells or NKX2.5-positive cells, that concentration X of XAV-939 is a concentration the increase of which will not further stimulate differentiation of the human pluripotent stem cell population in the absence of the second compound.

It was surprisingly found that under conditions that increase of the concentration of XAV-939 does not further stimulate and/or induce differentiation of the human pluripotent stem cell into cardiomyocytes, the addition of the second compound to XAV-939, in particular IWP-L6 could further stimulate differentiation of the cells, and for example, at least without negatively influencing yield and/or characteristics of the cardiomyocytes thus obtained.

As already discussed above, the in vitro method of the invention can be employed using all kinds of sources of the human pluripotent stem cells. Preferably, the human pluripotent stem cell population is a population of embryonic stem cells or a population of induced pluripotent stem cells. This may include established cell lines.

In some embodiments, the human pluripotent stem cells are prior to step a) cultured in a stem cell maintenance media, for example in the basic differentiation media as described above. In those embodiments wherein step a) is not performed, the human pluripotent stem cells may prior to step b) be cultured in a stem cell maintenance media, for example in the basic differentiation media as described above.

In some other embodiments, the cardiomyocyte population obtained from the human pluripotent stem cells are, after step b) or, in the given case, step c), are cultivated in a step d) in an aqueous media for maturing the cardiomyocyte cell population, preferably wherein the aqueous media comprises glucose, lipids, carnitine, creatine, taurine, optionally thyroid hormone analogs (T3 or DITPA, 3,5-diiodothyroproprionic acid) and optionally insulin, transferrin and selenium. Such media have for example been described in detail in WO2014200339.

For example, such composition comprises about 25 ng/ml to about 150 ng/ml of T3 and/or about 1 microM to about 2 microM of DITPA and/or comprises about 1 microgram/ml to about 4 microgram/ml of cholesterol, one or more lipids selected from linolenic acid, linoleic acid and palmitic acid (in concentrations as disclosed above), and/or about 0.5 mM to about 3.5 mM of carnitine, and/or about 3.0 mM to about 7.0 mM of creatine, and/or about 2 mM to about 7 mM of taurine, and/or about 5 mg/L to about 15 mg/L of insulin, and about 3 mg/L to about 8 mg/L of transferrin, and about 0.005 mg/L to about 0.0075 mg/L of selenium, and/or one or more trace elements, preferably all, selected from the group of Mn, Si, Mb, V, Ni, Sn, AL, Ag, Ba, K, Cd, Co, CR, F, Ge, I, Rb, and Zr; and/or wherein the composition further comprises bovine serum albumin, glucose, vitamins, antibiotics, monothiolglycerol, glutamine, amino acids, and Ham's F12 nutrient mix (e.g. Gibco 31765) and/or IMDM (e.g. Gibco 21056). Other suitable media may of course also be employed to further maturate the cells.

Preferably the method comprises prior to step d) that the cells have been harvested and frozen and kept in a suitable medium for storing frozen cells before re-plating/passaging the cells in the aqueous media for maturation in step d). Step d) is in a preferred embodiment performed within/for a period of 21 days, for example 1-21 days, preferably 4-18 days, preferably, 5-16 days.

In a preferred embodiment, the method of the invention, and wherein step d) is performed is concluded within a period of 50 days, preferably 35 days, even more preferably 30 days, even more preferably 21 days. For example the method of the invention, and wherein step d) is performed takes from 10-50 days, preferably from 11-35 days, even more preferable from 12-30 days, for example from 14-21 days.

It was surprisingly found that by performing step d) using a maturation medium for the cardiomyocytes, i.e. and wherein said medium is different from the media used prior to or during step a), and/or step b), and/or step c) high yields of well differentiated and matured cardiomyocytes, preferably ventricular cardiomyocytes, may be obtained.

In some embodiments the method of the invention further comprises the step of verifying the presence of cardiomyocytes, preferably ventricular cardiomyocytes, after step b), step c) and/or d). Such verifying may involve, for determining a cardiomyocyte electrophysiological profile; determining responsiveness to known cardioactive drugs; or analyzing the cell population for the presence or absence of specific cardiomyocyte marker proteins or genes such as TNNT2, Cardiac Troponin T, NKX2-5 (Homeobox protein Nkx-2.5 is a protein that in humans is encoded by the NKX2-5 gene) and/or mlc2v (myosin light chain (MLC) 2v) using conventional techniques.

For example, verifying the presence or metabolic maturity of cardiomyocytes, preferably ventricular cardiomyocytes, can be determined by methods known to the skilled person, for examples methods that look at phenotype, morphology, gene expression, metabolic markers, cell surface markers, electrophysiological characteristics and/or cellular functional assay of the cell.

For example, for verifying the presence of cardiomyocytes one can determine expression of genes associated with a "foetal" state or cardiac hypertrophyic state such as, for example, NPPA (BNA) and NPPB (BNP), or preferably, determine the electrophysiological characteristics of the maturing stem-cell derived cardiomyocytes, and wherein a more adult or adult-like cardiomyocyte characteristic can be seen for more maturated stem-cell derived cardiomyocytes.

Verifying the presence or maturity of cardiomyocytes, preferably ventricular cardiomyocytes, may also be determined by the presence or expression of genes associated with the a fetal state, such as NPPA, NPPB, smooth muscle actin and skeletal actin, or the expression of adult genes/proteins, such as myosin light chain 2V, calsequestrin and ryanodine receptor.

Verifying the phenotype of cardiomyocytes may also be determined by the presence or expression of genes associated with a certain subtype, such as MLC2v for ventricular cardiomyocytes and MLC2A and sarcolipin for atrial cardiomyocytes.

The skilled person knows how to assess the presence or maturity of stem cell derived cardiomyocytes in in vitro culture by using known cardiomyocyte-specific markers, e.g. ventricular cardiomyocyte-specific markers or lineage-specific markers relevant for a particular developmental stage as well as available methods in the art (see for example Burridge et al (2012), Stem Cell Cell, Vol. 10(1):16-28, US2013/0029368).

Another way is to assess the electrophysiological properties, for instance the ability of a cell to generate and/or propagate an action potential in vitro. Electrophysiological characteristics of cardiomyocytes, for example ventricular cardiomyocytes, in in vitro culture can be for instance assessed by patch clamp techniques, among other techniques, and may measure maximum upstroke velocity, resting membrane potential, and amplitude of the action potential, which are hallmarks of cardiomyocytes. Morphological features of a stem cell derived cardiomyocyte, for example ventricular cardiomyocytes, in in vitro culture can be for instance assessed by immunohistochemistry techniques (amongst other techniques), for instance using immunofluorescence (Cy3 or Alexa-Fluor 647) and antibodies directed against integral constituents of the cytoskeleton, for instance alpha-actinin.

In preferred embodiments of the method of the invention, at least 60%, 70%, 80%, 90% or 95% of the cells are determined to be cardiomyocytes, preferably ventricular cardiomyocytes, using conventional techniques.

Also provided are kits suitable for performing the method of the invention. There is provided for a kit for differentiating a human pluripotent stem cell population into a cardiomyocyte cell population preferably a ventricular cardiomyocyte cell population, the kit comprising
a) XAV939;
  a second compound, wherein the compound is IWP-L6 or C59;
  an aqueous media; and
  optionally IGF,
  preferably wherein the kit further comprises a Wnt-signaling agonist;
  preferably CHIR-99021 or
b) a first aqueous media comprising a Wnt-signaling agonist, preferably CHIR-99021;
  a second aqueous media comprising XAV-939 and the second compound wherein the compound is IWP-L6 or C59, preferably IWP-L6; and
  a third aqueous media that does not comprise XAV939, IWP-L6, C59 and a Wnt-signaling agonist,
  preferably wherein the kit further comprises a fourth aqueous media, wherein the fourth aqueous media is for maturation of in vitro obtained stem-cell derived cardiomyocytes.

Also provided is a cardiomyocyte cell population obtained with the method of the invention, preferably wherein the cardiomyocyte cell population resembles a human (fetal) ventricular cell population or wherein at least 70%, 80%, 90% or 95% of the cells express mlc2v. It was surprisingly found that with the method of the invention one may obtain with high yield and with a short period of time, for example within the periods as disclosed herein a population of human in vitro obtained stem-cell derived cardiomyocytes that display characteristics of human ventricular cardiomyocytes (as may be determined using conventional techniques known to the skilled person), in particular wherein the cells obtained express mlc2v. In vivo, MLC2v is strongly expressed in the ventricular myocardium and distinctly lower in the outflow tract and atrioventricular canal and is a bona fide marker of ventricular cardiomyocytes.

In particular is was found that when the method of the invention comprises step a), step b) and step d), even more preferably step a), step b), step c) and step d) a matured cardiomyocyte population is obtained wherein at least 70%, 80%, 90% or 95% of the cells express mlc2v. Prior to step d) the cells may be harvested and frozen in a suitable medium before plating and performing step d).

It was also found that when the media in step b) does not comprise vitamin A and/or derivatives thereof (e.g. retinoic acid, retinol, retinal, provitamin A carotenoids, and the like), cardiomyocytes, in particular ventricular cardiomyocytes, can be obtained.

It was further found that when the media in steps a), b) and/or c) does not comprise vitamin A and/or derivatives thereof (e.g. retinoic acid, retinol, retinal, provitamin A carotenoids, and the like), cardiomyocytes, in particular ventricular cardiomyocytes, can be obtained. In these embodiments, also step d) (if performed) may be performed with or without vitamin A and/or derivatives thereof (e.g. retinoic acid, retinol, retinal, provitamin A carotenoids, and the like).

In order words, there is also provided an in vitro method of differentiating a human pluripotent stem cell population into a cardiomyocyte cell population wherein at least 70, 80%, 90% or 95% of the cells express mlc2v, the method comprising performing step b), and step d) as defined herein, or performing step b), step c) and step d) as defined herein, or performing step a), step b) and step d) as defined herein, or performing step a), step b), step c) and step d) as defined herein. In a preferred embodiment, the in vitro method of differentiating a human pluripotent stem cell population into a cardiomyocyte cell population wherein at least 70, 80%, 90% or 95% of the cells express mlc2v is concluded within a period of 50 days, preferably 35 days, even more preferably 30 days, even more preferable 21 days. For example, the method takes from 10-50 days, preferably from 11-35 days, even more preferable from 12-30 days, for example from 14-21 days.

Also provided is an in vitro human cardiomyocyte cell population, preferably an in vitro human ventricular cardiomyocyte cell population, wherein at least 80%, 90% or 95% of the cells express mlc2v, preferably obtained with the method of the invention.

Having now generally described the invention, the same will be more readily understood through reference to the following examples which is provided by way of illustration and is not intended to be limiting of the present invention.

EXAMPLES

Method of Culturing the Cells

Human Pluripotent stem cells (hPSC) were cultured on feeders (mouse embryonic fibroblasts) with DMEM/F-12, GlutaMAX medium supplemented with 20% Knockout™ Serum Replacement, 1% NEAA, 10 ng/ml b-FGF, and 0.1 mM β-mercaptoethanol or under feeder-free conditions using Essential 8™ Medium (Life Technologies) on vitronectin (VTN-N) coated plates according to the manufacturer's instructions, or using L7 culture system (Lonza) according to manufacturer's instructions. Cells were routinely passaged using Accutase (Sigma-Aldrich) in case of feeder cultures or using 0.5 mM EDTA for E8 cultures or using L7 passaging solution in case of the L7 culture system. The cell cultures were maintained in a humidified incubator at 37° C. with 5% CO2. See, for example, http://hpscreg.eu/cell-line/CRMi003-A for NCRM-1 cells.

Methods for Differentiation

For differentiation, cells were seeded in 12-well plates at density of 60,000 cells per well or a split ratio that was empirically determined to give 30-80% confluence after 4 days. Culture media was replaced after 4 days with a differentiation media as disclosed herein, for example containing 46.5% IMDM (Gibco 21056), 0.25% Bovostar BSA, 46.5% Ham's F12 with Glutamax, 2 mM Glutamax, 450 nM alphaMTG, 0.05 mg/ml ascorbic acid, 0.5% 5000 U/ml Pen/Strep (Gibco 12070), 0.01% 1000* Trace elements mix B (Cellgro 99-176-CL), 0.1% 1000* Trace elements mix C (Cellgro 99-176-CL). In several experiments 0.1% ITS-x was used from day 4-14, i.e. during differentiation of the cells.

For maturation, a maturation media as disclosed herein was used.

Methods of Counting the Cells/Well

Cell numbers were determined with a Fuchs-Rosenthal counting chamber. Briefly, cells grown in monolayer cultures were detach from surface of plate using TrypLE™ Select Enzyme (Life Technologies). A uniform cell suspension was transferred to the edge of hemocytometer counting chamber. Cells were counted and number of cells was determined using following equations:

cells/ml=average count per square×dilution factor×5000 total cells=cells/ml×total original volume of cell suspension from which sample was taken.

Method of Measuring NKX2.5

NKX-GFP reporter hESC and iPSC cells have been described previously. These cells express the fluorescent protein GFP under the control of the endogenous NKX2-5 promoter. GFP+ve cells mark cardiomyocytes (Elliott D A et al. Nat. Methods, 8 (2011), pp. 1037-1040; van den Berg C W et al., Development. 2015 Jul. 24. pii: dev.123810. [Epub ahead of print]). NKX 2.5 is transcription factor essential for heart development and it is expressed in the heart throughout life. GFP fluorescence reports the expression of the endogenous NKX2.5 gene and enables identification/quantification of hPSC-derived cardiomyocytes during differentiation.

Method of Measuring TNNT2 (Using FACS)

The percentage TNNT2 expressing cells was measured by flow cytometric analysis. Briefly, cells were dissociated with TrypLE™ Select Enzyme (Life Technologies), washed with PBS, fixed and permeabilized with FIX & PERM® Cell Fixation and Permeabilization Kit (Life Technologies). Samples were incubated with Troponin T (TNNT2), Cardiac Isoform Ab-1, Mouse Monoclonal Antibody (ThermoFisher, MS-295-P1; at 1:1000 dilution) followed by incubation with secondary antibody Donkey Anti-mouse APC (Jackson Immuno, 715-136-151; at 1:500 dilution) both diluted in Fix&Perm Medium B. Samples were analyzed on a Novocyte™ Flow Cytometer (ACEA Biosciences) or a MACSQuant VYB instrument (Miltenyi Biotech).

Method of Measuring MLC2v & Troponin

Mcl2v is specific for ventricular cells while Cardiac Troponin T (TNNT2) is expressed both in atrial and ventricular cells. Mlc2v and TNNT2 were measured by flow cytometric analysis as mentioned above. The percentage TNNT2 and Mlc2v expressing cells was measured by flow cytometric analysis. Cells were dissociated with TrypLE™ Select Enzyme (Life Technologies), wash with PBS, fix and permeabilized with FIX & PERM® Cell Fixation and Permeabilization Kit (Life Technologies). Samples were incubated with Troponin T, Cardiac Isoform Ab-1, Mouse Monoclonal Antibody (ThermoFisher, MS-295-P1; at 1:1000 dilution) and Rabbit-anti-MLC2V Ab (ProteinTech 10906-1-AP; at 1:200 dilution) followed by incubation with secondary antibodies Donkey Anti-mouse APC (Jackson Immuno, 715-136-151; at 1:500 dilution) and Anti-Rabbit-AlexaFluor488 Ab (Life Technologies A21206; at 1:500 dilution) diluted in Fix&Perm Medium B (Life Technologies). Samples were analyzed on a Novocyte™ Flow Cytometer (ACEA Bioscicences) or a MACSQuant VYB instrument (Miltenyi Biotech).

RESULTS

FIG. 1 shows an example schematic overview of an embodiment of the method of the invention.

Figure 2:
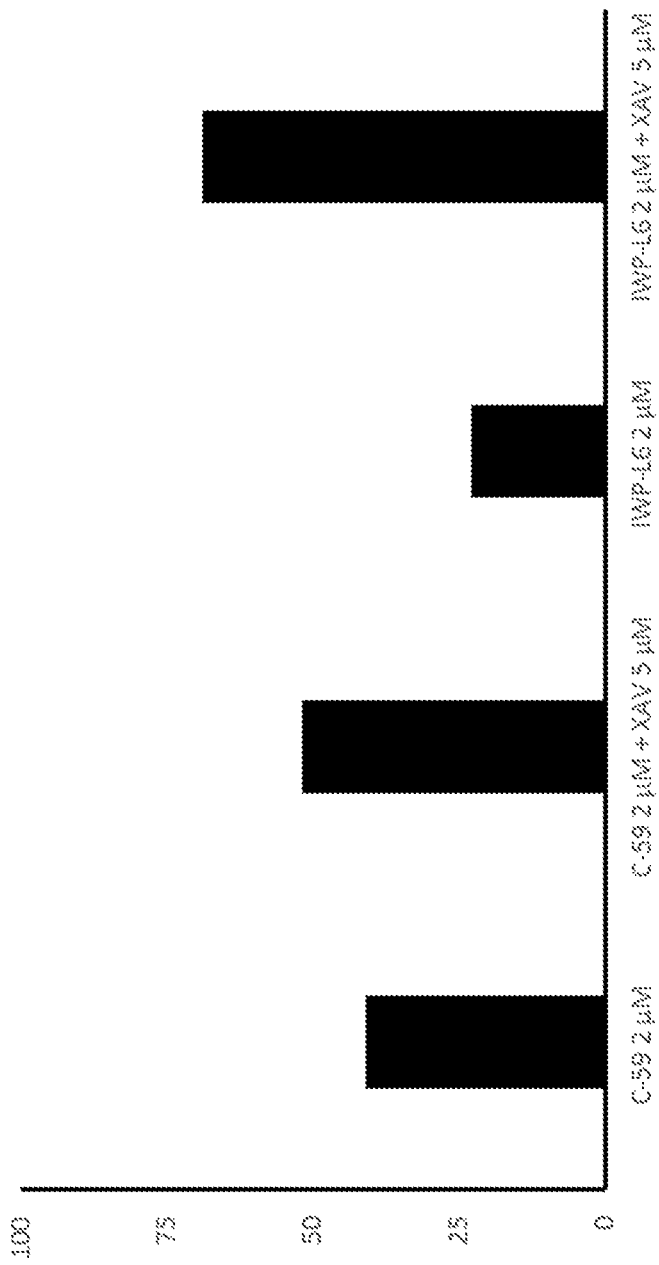

FIG. 2 shows exemplary results of experiments studying the effects of wnt inhibitors on the differentiation of the stem cells. For the data in the figure, NKX2-5-GFP reporter stem cells were cultured on feeders in KOSR/bFGF supplemented DMEM-F12 (Amit, M. et al. (2004) Biol Reprod 70, 837-45.). NKX-GFP reporter hESC and iPSC cells have been described previously. These cells express the fluorescent protein GFP under the control of the endogenous NKX2-5 promoter. GFP+ve cells mark cardiomyocytes (Elliott D A et al. Nat. Methods, 8 (2011), pp. 1037-1040; van den Berg C W et al., Development. 2015 Jul. 24. pii: dev.123810. [Epub ahead of print]). To start differentiation, cells were dissociated using Accutase and resuspended in mTesR (StemCell Technologies; Ludwig T E et al. Nat Methods 3: 637-46, 2006) at a concentration of 60,000/ml cells, the cell suspension was seeded onto Matrigel coated 12-well plates. Cells were maintained for 4 days before onset of differentiation. Cells were treated for 2 days with 5 microMolar CHIR99021, followed by 2 days culture in the presence of IWP-L6/XAV-939 (or C59/IWPL-6), next the cells were cultured for 10 days in the differentiation medium in the absence of the Wnt inhibiting small molecules. Percentage of cardiomyocytes was determined at day 14 of differentiation using flow cytometry for detection/quantification of GFP positive cells. The combination of IWP-L6 and XAV is the most effective. It has been observed that measurement of GFP expression cells gives an underestimation of percentage TNNT2 cells.

FIG. 3 shows exemplary results studying the effects of wnt inhibitors on the differentiation of the stem cells. Here, NKX2-5-GFP reporter stem cells were cultured on feeders in KOSR/FGF supplemented DMEM-F12. To start differentiation, cells were dissociated using Accutase and resuspended in mTesR at a concentration of 60,000/ml cells, the cell suspension was seeded onto Matrigel coated 12-well plates. Cells were maintained for 4 days before onset of differentiation. Cells were treated for 2 days with 5 microMolar CHIR99021, followed by 2 days culture in the presence of specified wnt inhibiting small molecules, next the cells were cultured for 10 days in differentiation medium. Percentage of cardiomyocytes was determined at day 14 of differentiation using flow cytometry for detection/quantification of GFP positive cells. The results show that reduction of IWP-L6 from 2 microMolar to 0.25 microMolar increases the differentiation efficiency even further. It has been observed that measurement of GFP expression cells gives an underestimation of percentage TNNT2 cells.

Figure 4A:
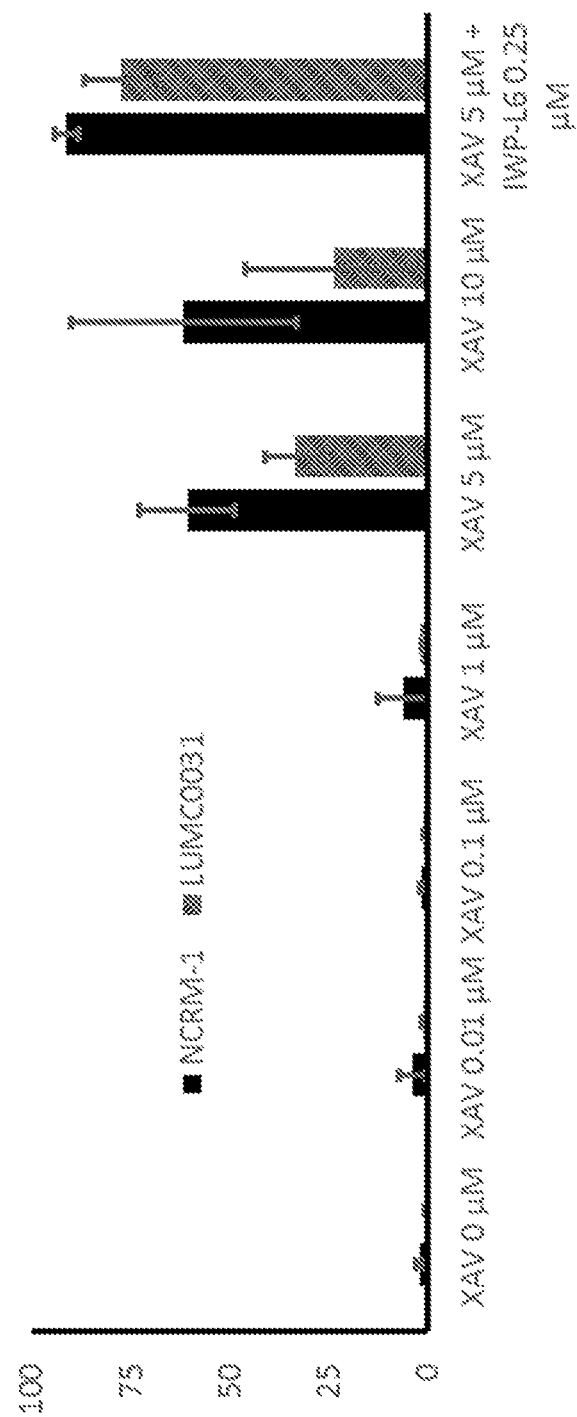
Figure 4B:
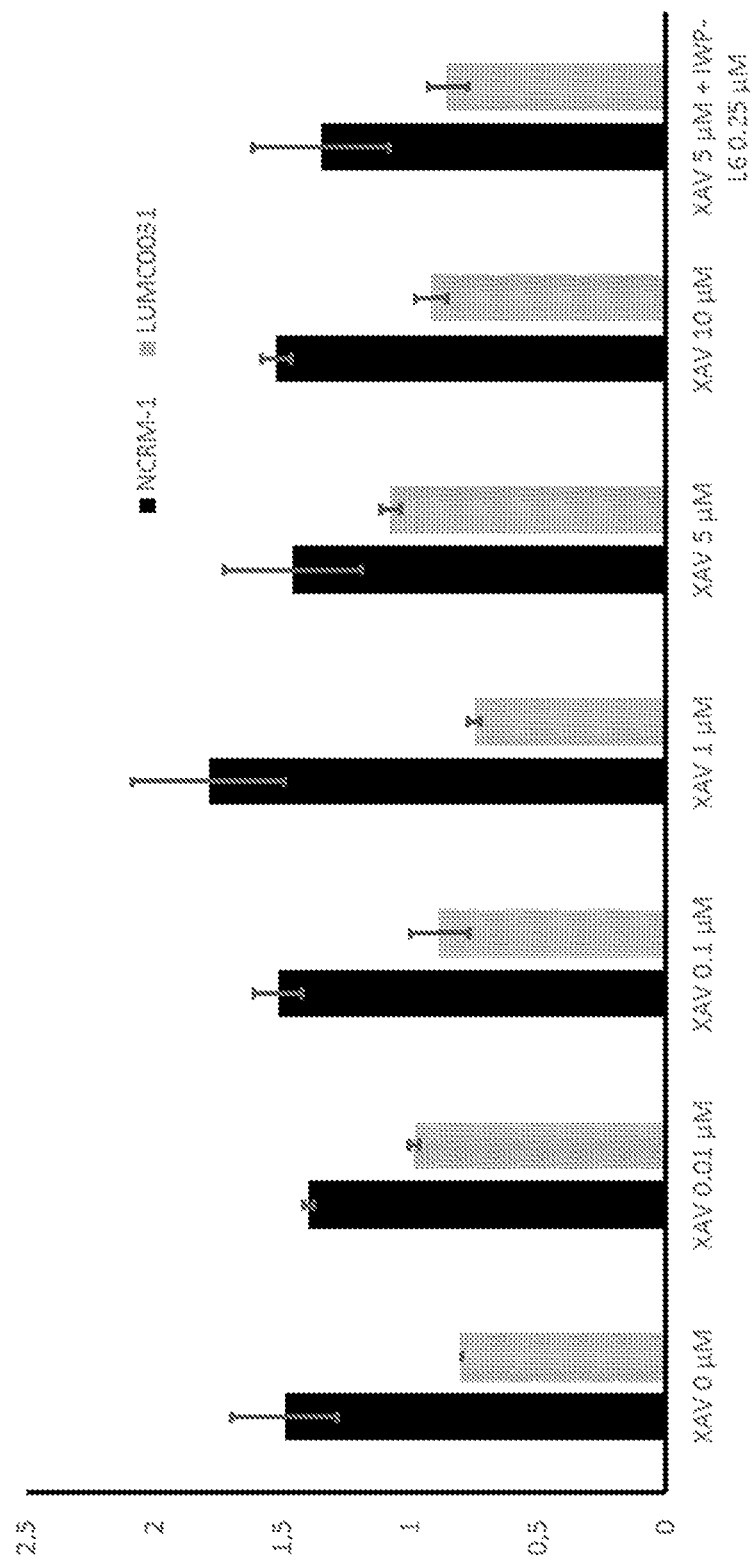

FIG. 4 shows titration of XAV-939 and the effects on differentiation. Two hIPSC lines were cultured on feeders in KOSR (InvitroGen)/FGF supplemented DMEM-F12. To start differentiation, cells were dissociated using Accutase and resuspended in mTesR at a concentration of 60,000/ml cells, the cell suspension was seeded onto Matrigel coated 12-well plates. Cells were maintained for 4 days before onset of differentiation. Cells were treated for 2 days with 5 microMolar CHIR99021, followed by 2 days culture in the presence of specific Wnt inhibiting small molecules, next the cells were cultured for 10 days in differentiation medium. Percentage of cardiomyocytes (FIG. 4A; % TNNT2 positive cells at day 14) was determined at day 14 of differentiation using flow cytometry for the pan-cardiac marker Troponin-T (TNNT-2). Data confirms that XAV939 at 5 microMolar is an optimal concentration, further increase of concentration reduces differentiation efficiency. Addition of IWP-L6 at 0.25 microMolar further improves the differentiation even further. Presence and absence or concentration have no significant effect on the total number of cells (FIG. 4B; cell count at day 14, in million cells/well).

Figure 5:
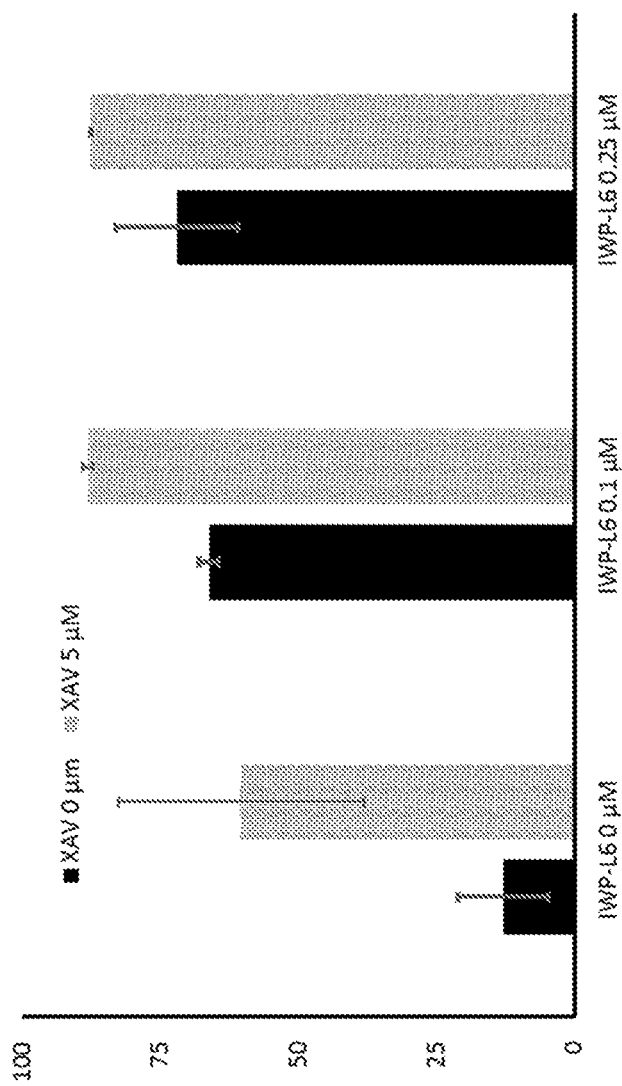

FIG. 5 shows the effect of wnt inhibitors on performance of the differentiation system. Human IPSC lines were cultured on feeders in KOSR/FGF supplemented DMEM-F12. To start differentiation, cells were dissociated using Accutase and resuspended in mTesR at a concentration of 60,000/ml cells, the cell suspension was seeded onto Matrigel coated 12-well plates. Cells were maintained for 4 days before onset of differentiation. Cells were treated for 2 days with 5 microMolar CHIR99021, followed by 2 days culture in the presence of specific wnt inhibiting small molecules, next the cells were cultured for 10 days in differentiation medium. Percentage of cardiomyocytes was determined at day 14 of differentiation using flow cytometry for the pan-cardiac marker Troponin-T (TNNT-2). Here, IWP-L6 alone gives a differentiation efficiency of about 70% this is further increased by the addition of XAV939.

Figure 6:
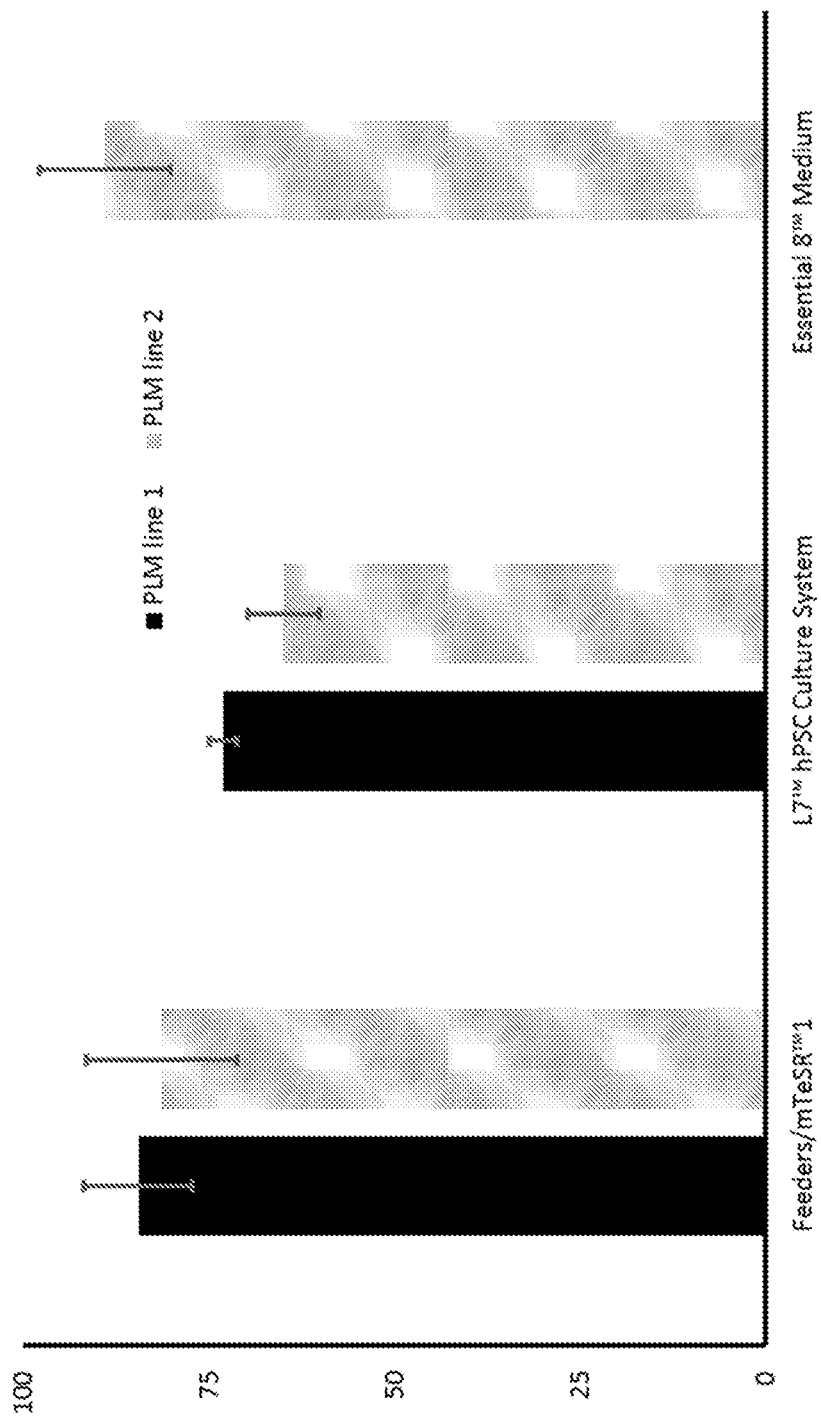

FIG. 6 shows the differentiation performance using different hiPSC maintenance systems. A panel of up to 2 hiPSC lines was used to test performance of the cardiac differentiation system. Cells were maintained on feeders (Amit, M. et al. (2004). Biol Reprod 70, 837-45.), L7 culture medium (Lonza; www.lonza.com/products-services/bio-research/stem-cells/pluripotent-stem-cells/pluripotent-stem-cells-and-media/l7-hipsc-reprogramming-and-hpsc-culture-system/l7-culture-system.aspx) or Essential 8 culture medium (Thermo Fisher Scientific; Chen G. et al. Nat Methods 8(5):424-429, 2011; www.thermofisher.com/order/catalog/product/A1517001; tools.thermofisher.com/content/sfs/manuals/feeder_free_PSCs_in_essential8_medium.pdf). Cells from all three maintenance systems were pre-cultured for 4 days prior to differentiation. Cells were treated for 2 days with 5 microMolar CHIR99021, 2 days with a combination of 5 microMolar XAV939 and 0.25 microMolar IWP-L6 followed by 10 days culture in differentiation medium. Percentage of cardiomyocytes was determined at day 14 of differentiation using flow cytometry for the pan-cardiac marker Troponin-T (TNNT-2).

Surprisingly, despite the wide range of hIPSC maintenance methods tested the results are highly consistent between experimental conditions confirming the robustness of the method (PLM 2 is NCRM1).

Figure 7A:
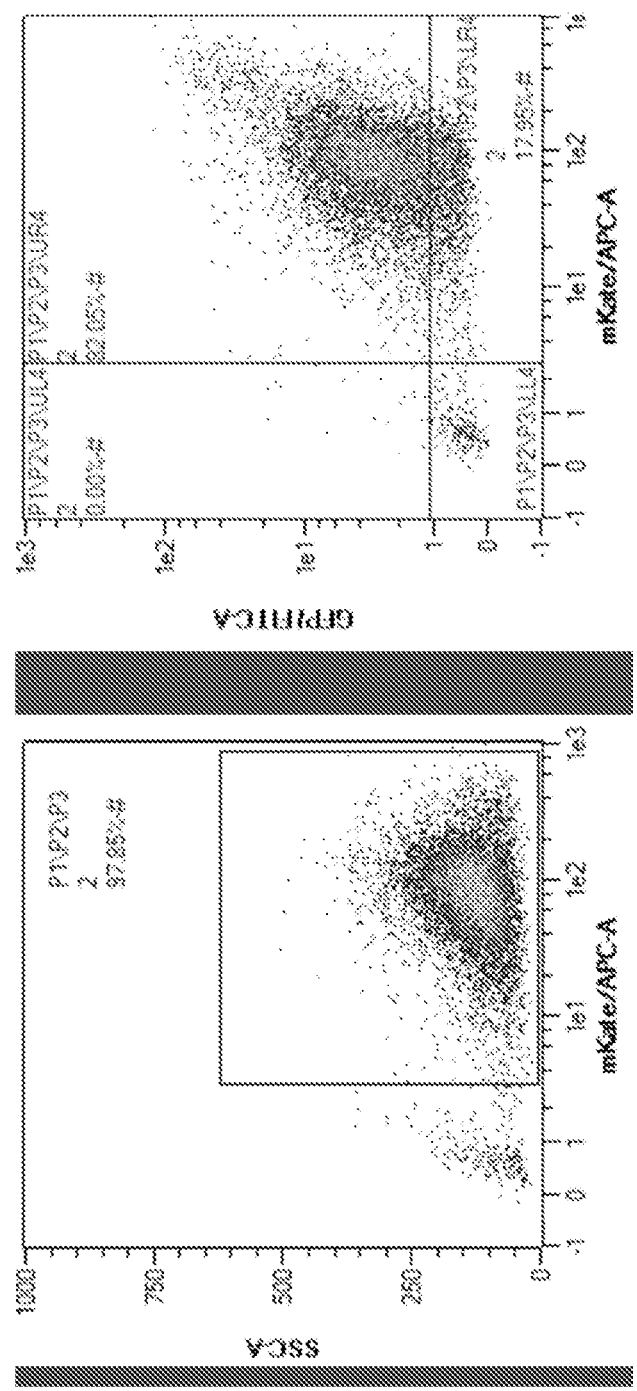
Figure 7B:
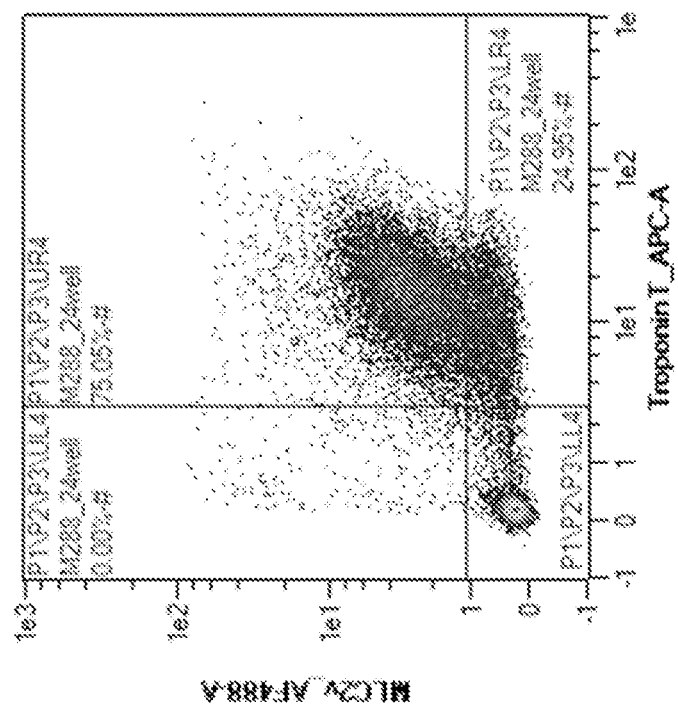
Figure 7B:
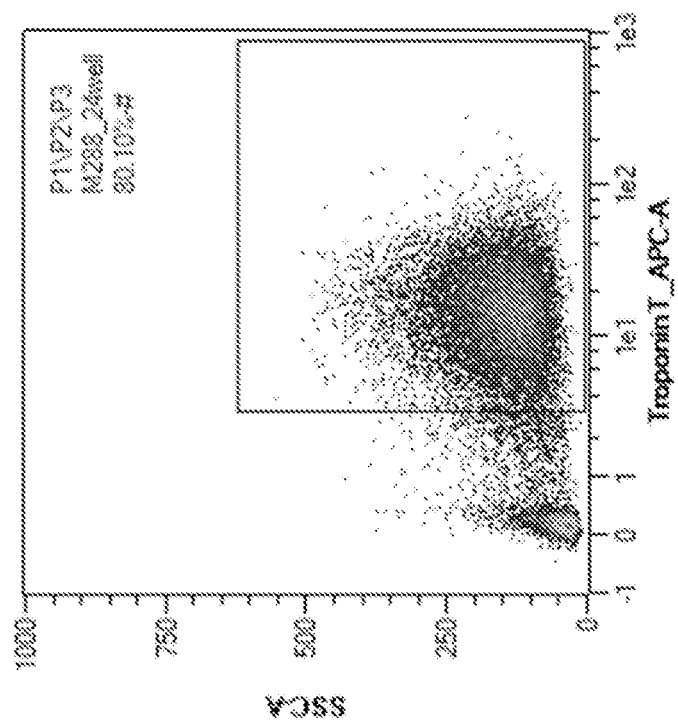

FIG. 7 shows hPSC-CM differentiated from (A) PLM line 1 and (B) NCRM-1 hiPSC. hIPSC lines were cultured on feeders in KOSR/FGF supplemented DMEM-F12. To start differentiation, cells were dissociated using Accutase and resuspended in mTesR at a concentration of 60,000/ml cells, the cell suspension was seeded onto Matrigel coated 12-well plates. Cells were maintained for 4 days before onset of differentiation. Cells were treated for 2 days with 5 micro-Molar CHIR99021, followed by 2 days culture in the presence of specific wnt inhibiting small molecules IWPL-6/XAV939, next the cells were cultured for 10 days in differentiation medium. Cells were dissociated at day 14 and cryopreserved. Cells were thawed and replated in maturation medium as disclosed herein and cultured for 7 days (day 14+7). Cardiomyocytes were characterized using flow cytometry with the pan-cardiac marker Troponin-T (TNNT-2) and the ventricular marker MLC2v.

Cells are predominantly of the ventricular subtype as shown by expression of ventricular marker Mlc2v. For PLM line 1, an efficiency of 97.85% of TNNT2+ cells was obtained and 82% of this population was Mlc2v % +. For NCRM-1, an efficiency of 80.10% of TNNT2+ cells was obtained and 82% of this population was 75.05% Mlc2v % +.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding patent applications, patents, or any other references, are entirely incorporated by reference herein, including all data, tables, figures, and text presented in the cited references. Additionally, the entire contents of the references cited within the references cited herein are also entirely incorporated by references./nlp Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

The invention claimed is:

1. An in vitro method for use in differentiating a human pluripotent stem cell population into a cardiomyocyte cell population, the method comprising:
    a) contacting the human pluripotent stem cell population with XAV-939 and IWP-L6 in an aqueous media.

2. The method of claim 1, wherein the method further comprises
    b) contacting, prior to step a), the human pluripotent stem cell population with at least a Wnt-signaling agonist in an aqueous media.

3. The method of claim 1, wherein the method further comprises contacting the human pluripotent stem cell population with IGF.

4. The method of claim 2, wherein the method further comprises
    c) contacting, after step a), the human pluripotent stem cell population with an aqueous media devoid of XAV-939, IWP-L6, and said Wnt-signaling agonist.

5. The method of claim 2, wherein the aqueous media of each of steps a) and b) is essentially serum-free.

6. The method of claim 1, wherein said step a) is concluded within 35 days after its initiation.

7. The method of claim 4, wherein step c) is concluded within 35 days after its initiation.

8. The method of claim 1, wherein
    the concentration XAV-939 is 0.1-20 microM in the aqueous media; or
    the concentration IWP-L6 is 0.01-15 microM in the aqueous media.

9. The method of claim 1, wherein the ratio XAV-939:IWP-L6 is between 1:1 and 1:0.001.

10. The method of claim 1, wherein the concentration of XAV-939 with which the human pluripotent stem cell population are contacted in step a) is a concentration, the increase of which will not further stimulate differentiation of the human pluripotent stem cell population in the absence of IWP-L6.

11. The method of a claim 2, wherein the human pluripotent stem cell population is a population of embryonic stem cells or a population of induced pluripotent stem cells.

12. The method of claim 4, wherein the method further comprises, after said step c),
    d) culturing the cardiomyocyte cell population in an aqueous media for maturing the cardiomyocyte cell population.

13. The method of claim 1, wherein the media of step a) does not contain vitamin A and/or a derivative thereof.

14. The method of claim 2, wherein step a) is initiated at least 1 and up to 7 days after initiation of step b).

15. The method of claim 2, wherein the aqueous media of each steps a) and b) comprises lipids and one or more trace elements.

16. The method of claim 4, wherein the aqueous media of each of steps a), b) and c) comprises insulin, transferrin and selenium.

17. The method according to claim 12, wherein the aqueous media of step d) comprises at least glucose, lipids, carnitine, creatine, and taurine.

18. The method of claim 2, wherein the aqueous media of step b) does not contain vitamin A and/or a derivative thereof.

19. The method of claim 4, wherein the aqueous media of step c) does not contain vitamin A and/or a derivative thereof.

20. The method of claim 3, wherein the concentration IGF is 0.01-10 ng/ml in the aqueous media.

21. The method of claim 2, wherein the method further comprises, after said step a),
   d) culturing the cardiomyocyte cell population in an aqueous media for maturing the cardiomyocvte cell population.

22. The method according to claim 21, wherein the aqueous media of step d) comprises at least glucose, lipids, carnitine, creatine, and taurine.

23. The method of claim 1, wherein
   the concentration XAV-939 is 0.1-20 microM in the aqueous media; and
   the concentration IWP-L6 is 0.01-15 microM in the aqueous media.

24. The method of claim 2, wherein neither the aqueous media of step b) nor the aqueous media of step a) contains vitamin A and/or a derivative thereof.

25. The method of claim 4, wherein neither the aqueous media of step b) nor the aqueous media of step a) nor the aqueous media of step c) contains vitamin A and/or a derivative thereof.

26. The method of claim 12, further including, after step c) and prior to step d), harvesting and freezing the cells, and then thawing for use in step d).

27. The method of claim 21, further including, after step a) and prior to step d), harvesting and freezing the cells, and then thawing for use in step d).

28. The method according to claim 4, wherein the aqueous media of step c) comprises IGF.

* * * * *